US012084681B2

(12) United States Patent
Van Helden et al.

(10) Patent No.: US 12,084,681 B2
(45) Date of Patent: Sep. 10, 2024

(54) EX VIVO ANTIBODY PRODUCTION

(71) Applicant: KLING BIOTHERAPEUTICS B.V., Amsterdam (NL)

(72) Inventors: Paula Maria Wilhelmina Van Helden, Amsterdam Zuidoost (NL); Mark Jeroen Kwakkenbos, Amsterdam Zuidoost (NL); Hergen Spits, Amsterdam Zuidoost (NL); Tim Beaumont, Amsterdam Zuidoost (NL)

(73) Assignee: KLING BIOTHERAPEUTICS B.V., Amsterdam (NL)

( * ) Notice: Subject to any disclaimer, the term of this patent is extended or adjusted under 35 U.S.C. 154(b) by 600 days.

(21) Appl. No.: 16/575,518

(22) Filed: Sep. 19, 2019

(65) Prior Publication Data
US 2020/0149007 A1 May 14, 2020

Related U.S. Application Data

(62) Division of application No. 15/106,991, filed as application No. PCT/NL2014/050908 on Dec. 24, 2014, now abandoned.

(30) Foreign Application Priority Data

Dec. 24, 2013 (EP) ..................................... 13199584

(51) Int. Cl.
C12N 5/0781 (2010.01)
A61K 38/00 (2006.01)
C07K 16/00 (2006.01)
C07K 16/10 (2006.01)
C12N 15/06 (2006.01)
C12N 15/86 (2006.01)
C12P 21/00 (2006.01)

(52) U.S. Cl.
CPC ............ *C12N 5/0635* (2013.01); *C07K 16/00* (2013.01); *C07K 16/1018* (2013.01); *C12N 15/86* (2013.01); *C12P 21/005* (2013.01); *C07K 2317/14* (2013.01); *C12N 2510/00* (2013.01); *C12N 2510/02* (2013.01); *C12N 2510/04* (2013.01); *C12N 2740/13045* (2013.01); *C12N 2810/6054* (2013.01)

(58) Field of Classification Search
None
See application file for complete search history.

(56) References Cited

U.S. PATENT DOCUMENTS

| | | | |
|---|---|---|---|
| 9,127,251 B2 | 9/2015 | Spits et al. | |
| 9,273,118 B2 | 3/2016 | Beaumont et al. | |
| 2013/0331552 A1 | 12/2013 | Beaumont et al. | |
| 2017/0008952 A1* | 1/2017 | Kwakkenbos | ....... C12Q 1/6869 |
| 2019/0153091 A1* | 5/2019 | Endl | ..................... C12N 5/0635 |

FOREIGN PATENT DOCUMENTS

| | | |
|---|---|---|
| WO | 2003/091442 A1 | 11/2003 |
| WO | 2007/019223 A1 | 2/2007 |
| WO | 2007067046 A1 | 6/2007 |
| WO | 2013076139 A1 | 5/2013 |
| WO | 2014/109696 A1 | 7/2014 |

OTHER PUBLICATIONS

Vaeck et al ( Europ.J of Immunol, 1982,v.12, pp. 953-960.*
Kwakkenbos, Mark J., et al.; Generation of stable monoclonal antibody-producing B cell receptor-positive human memory B cells by genetic programming; Nature Medicine, vol. 16, No. 1, Jan. 1, 2010, pp. 123-128.
Akatsuka, Y., et al.; Efficient cloning and expression of HLA class I cDNA human B-lymphoblastoid cell lines; Tissue Antigens, Jun. 1, 2002, pp. 502-511.
Mock, Ulrike, et al.; Efficient Lentiviral Transduction and Transgene Expression in Primary Human B Cells; Human Gene Therapy Methods, vol. 23, No. 6, Dec. 1, 2012, pp. 408-415.
Ting, Yuan-Tsang, et al.; Simian Sarcoma-Associated Virus Fails To Infect Chinese Hamster Cells despite the Presence of Functional Gibbon Ape Leukemia Virus Receptors; Journal of Virology, The American Society for Microbiology, US, vol. 72, No. 12, Dec. 1, 1998, pp. 9453-9458.
Huifeng, Niu; The Proto-Oncogene BCL-6 in Normal and Malignant B Cell Development: Hematological Oncology, vol. 20, No. 4, Jan. 1, 2002, pp. 155-166.
International Search Report and Written Opinion, dated Nov. 24, 2015, issued in PCT/NL2014/050908.
Feng, L., et al.; Rabbit monoclonal antibody: potential application in cancer therapy: American Journal of Translational Research 2011, vol. 3, No. 3, pp. 269-274.
Hanger, J., et al.; The Nucleotide Sequence of Koala (Phascolarctos cinereus) Retrovirus: a Novel Type C Endogenous Virus Related to Gibbon Ape Leukemia Virus; Journal of Virology, vol. 74, No. 9; May 1, 2000, pp. 4264-4272.
Christopherson, K.S., et al.; Ecdysteroid-dependent regulation of genes in mammalian cells by a *Drosophila* ecdysone receptor and chimeric transactivators; PNAS 89, 1992, pp. 6314-6318.
Guzman, L.M., et al.; Tight Regulation, Modulation, and High-Level Expression by Vectors Containing the Arabinose PBAD Promoter; Bacteroil 177. 1995, pp. 4121-4130.
Kinsella, T.M., et al.; Episomal Vectors Rapidly and Stably Produce High-Titer Recombinant Retrovirus; Human Gene Therapy 7 (1996), pp. 1405-1413.
Lam, J.S., et al.; Improved Gene Transfer into Human Lymphocytes Using Retroviruses with the Gibbon Ape Leukemia Virus Envelope; Human Gene Therapy 7 (1996), pp. 1415-1422.

(Continued)

*Primary Examiner* — Michail A Belyavskyi
(74) *Attorney, Agent, or Firm* — Gianna Julian Arnold; Saul Ewing LLP

(57) ABSTRACT

The present invention provides means and methods for producing improved ex vivo B cell cultures with a short doubling time.

19 Claims, 11 Drawing Sheets

Specification includes a Sequence Listing.

(56) References Cited

OTHER PUBLICATIONS

Szymczak, A.L., et al.; Correction of multi-gene deficiency in vivo using a single 'self-cleaving' 2A peptide-based retroviral vector; Nature Biotechnology 22 (2004), pp. 589-594.

Wilson, C.A., et al.; The Dual-Function Hamster Receptor for Amphotropic Murine Leukemia Virus (MuLV), 10A1 MuLV, and Gibbon Ape Leukemia Virus is a Phosphate Symporter; Journal of Virology 69 (1995), pp. 534-537.

Spieker-Polet, H., et al.; Rabbit monoclonal antibodies: Generating a fusion partner to produce rabbit-rabbit hybridomas; Proc. Natl. Acad. Sci. USA, Sep. 1995, vol. 92, pp. 9348-9352.

Coffin, JM, et al.; Receptors—Retroviruses—NCBI Bookshelf; Cold Spring Harbor (NY): Cold Spring Harbor Laboratory Press; 1997, pp. 1-15.

Coffin, JM, et al.; Principles of Retroviral Vector Design; Retrovirus—NCBI Bookshelf; Cold Spring Harbor (NY): Cold Spring Harbor Laboratory Press; 1997, pp. 1-22.

Coffin, JM, et al,.; Table 2, Host Range of Vectors with Various Pseudotypes; Retrovirus—NCBI Bookshelf; Cold Spring Harbor (NY): Cold Spring Harbor Laboratory Press; 1997, p. 1.

Opferman, J., et al.; Development and maintenance of B and T lymphocytes requires antiapoptotic MCL-1; Nature, Dec. 2003, vol. 426, pp. 571-576.

Office Action (and English Translation thereto), dated Dec. 15, 2019, and English translation thereof issued in corresponding Chinese Application No. 20148007624.X.

Office Action (and English Translation thereto), dated Nov. 18, 2019, and English translation thereof issued in corresponding Japanese Application No. 2016-542681.

Olah, Z., et al.; The Cellular Receptor for Gibbon Ape Leukemia Virus Is a Novel High Affinity Sodium-dependent Phosphate Transporter; The Journal of Biological Chemistry, Oct. 14, 1994, vol. 269, No. 41, pp. 25426-25431.

Miller, A. Dusty, et al.; Construction and Properties of Retrovirus Packaging Cells Based on Gibbon Ape Leukemia Virus; Journal of Virology, May 1991, vol. 65, No. 5, pp. 2220-2224.

Office Action dated Feb. 28, 2020 issued in corresponding Australian Application No. 2014370516.

Kwakkenbos, M., et al.; Genetic manipulation of B cells for the isolation of rare therapeutic antibodies from the human repertoire; Methods, Academic Press, NL, vol. 65, No. 1, Jul. 15, 2013, pp. 38-43, XP002719156.

Kwakkenbos, M., et al.; Stable long-term cultures of self-renewing B cells and their applications; Immunological Reviews, Wiley-Blackwell Publishing, Inc., US, vol. 270, No. 1, Feb. 10, 2016, pp. 65-77, XP071456205.

European Search Report, dated Jan. 17, 2023, issued in corresponding European Application No. 22194685.

* cited by examiner

Identification of antigen-specific rabbit B-cells within a pool of rabbit B cells with different specificities.

Supernatant of rabbit B cells cultured at different cell densities was tested for specificity against influenza vaccine antigens

| No. of cells/well | Total cell no. | Rabbit 1 Positive wells (frequency %) | Rabbit 2 Positive wells (frequency %) |
|---|---|---|---|
| 100 | 38400 | 95 (0.25) | 326 (0.85) |
| 25 | 19200 | 39 (0.20) | >80* |
| 10 | 11520 | 25 (0.22) | 114 (0.99) |
| 1 | 2304/1920 | 5 (0.22) | 22 (1.15) |

FIG. 5

Supernatant of rabbit B cells antigen-sorted and cultured one cell per well was tested for specificity of different compounds of the influenza vaccine; antigen sorting greatly facilitates isolation of antigen-specific cells

| Rabbit | Antigen used for sorting | Nr wells analyzed | H1-specific | H3-specific | B-specific | Frequency of clones antigen-specific (%) |
|---|---|---|---|---|---|---|
| 1 | H1 | 54 | 30 | | | 56 |
| 1 | H3 | 74 | | 17 | | 23 |
| 1 | B | 75 | | | 8 | 11 |
| 2 | H1 | 78 | 53 | | | 68 |
| 2 | H3 | 93 | | 60 | | 65 |
| 2 | B | 60 | | | 16 | 27 |

FIG. 6

MVLLPGSMLLTSNLHHLRHQMSPGSWKRLIILLSCVFGGGGTSLQNKNPHQPMTLTWQVLSQTGDVV
WDTKAVQPPWTWWPTLKPDVCALAASLESWDIPGTDVSSSKRVRPPDSDYTAAYKQITWGAIGCSYPR
ARTRMASSTFYVCPRDGRTLSEARRCGGLESLYCKEWDCETTGTGYWLSKSSKDLITVKWDQNSEWTQ
KFQQCHQTGWCNPLKIDFTDKGKLSKDWITGKTWGLRFYVSGHPGVQFTIRLKITNMPAVAVGPDLVL
VEQGPPRTSLALPPPLPPREAPPPSLPDSNSTALATSAQTPTVRKTIVTLNTPPPTGDRLFDLVQGAFL
TLNATNPGATESCWLCLAMGPPYYEAIASSGEVAYSTDLDRCRWGTQGKLTLTEVSGHGLCIGKVPFTH
QHLCNQTLSINSSGDHQYLLPSNHSWWACSTGLTPCLSTSVFNQTRDFCIQVQLIPRIYYPEEVLLQAY
DNSHPRTKREAVSLTLAVLLGLGITAGIGTGSTALIKGPIDLQQGLTSLQIAIDADLRALQDSVSKLEDSL
TSLSEVVLQNRRGLDLLFLKEGGLCAALKEECCFYIDHSGAVRDSMKKLKEKLDKRQLERQKSQNWYE
GWFNNSPWFTTLLSTIAGPLLLLLLLILGPCILN*RLVQFVKDRISVVQALVLTQQYHQLKPIEYEP*

SEQ ID NO. 4

FIG. 9

EX VIVO ANTIBODY PRODUCTION

CROSS REFERENCE TO RELATED APPLICATIONS

This application is a divisional of Ser. No. 15/106,991 filed on Jun. 21, 2016, and PCT/NL2014/050908, filed on Dec. 24, 2014, which claims priority to EP Application No. 13199584.7, filed Dec. 24, 2013, the entire contents of each of which are hereby incorporated in total by reference.

FIELD

The invention relates to the fields of medicine, molecular biology and immunology.

SEQUENCE LISTING

This application incorporates by reference the Sequence Listing contained in an ASCII text file named "362346_00056_Sequence.txt" submitted via EFS-Web. The text file was created on Jan. 29, 2020 and is 13 kb in size.

BACKGROUND

Ex vivo B cell cultures are important tools for producing antibodies, preferably monoclonal antibodies. Monoclonal antibodies (mAbs) represent multiple identical copies of a single antibody molecule, which copies bind to antigens with the same affinity and promote the same effector functions. Amongst the benefits of mAbs is their specificity for the same epitope on an antigen. This specificity confers certain clinical advantages on mAbs over more conventional treatments while offering patients an effective, well-tolerated therapy option with generally low side effects. Moreover mAbs are useful for biological and medical research.

A conventional approach for obtaining mAbs is hybridoma technology, wherein a B cell is fused with a myeloma cell in order to form hybrid antibody producing cell lines (hybridomas). However, hybridoma technology with human B cells has not been very successful because the resulting hybridomas are unstable. Meanwhile, an improved technology has been developed wherein ex vivo B cell cultures are produced with a prolonged replicative life span (WO 2007/067046). This technology involves human ex vivo cultures wherein Bcl-6, together with Blimp-1 and/or an anti-apoptotic nucleic acid, are expressed in the B cells. This improves the replicative life span of these B cells. Typically, human B cells are cultured in order to obtain human mAbs. Human mAbs are preferred for therapeutic applications in humans due to the lower immunogenicity as compared to antibodies of other species. Using the technology of WO 2007/067046, ex vivo human B cell cultures with a mean doubling time of about 25-36 hours are obtained.

In order to commercially produce mAbs of interest, such as therapeutic mAbs, it is advantageous to use B cell cultures wherein the B cells have a short doubling time. A short doubling time is also very important in therapeutic approaches like cancer therapy, for instance when a non-human mammal is immunized with cancer cells of a patient, where after cancer-specific B cells are harvested from the animal and used for ex vivo antibody production. Since such antibodies are a tailor-made medicine for the individual patient, they should be produced as fast as possible so that the patient can start his/her Ab therapy as soon as possible. Such antibodies that are specific for an individual's tumor cannot be produced beforehand.

It is one of the objects of the present invention to provide means and methods for producing improved ex vivo B cell cultures with a shorter doubling time.

The present invention provides the insight that B cell cultures with a shorter doubling time, as compared to the B cell cultures disclosed in WO 2007/067046, are obtained when rabbit B cells are used. Whereas commonly used B cells such as human B cells, murine B cells and llama B cells typically have a doubling time of 25-36 hours, the present inventors have surprisingly found that rabbit B cell cultures can be obtained with a doubling time of 20 hours or less. This insight allows significant faster production of antibodies of interest, resulting in a higher yield within a given time frame, which is particularly valuable for commercial antibody production and therapeutic applications.

Accordingly, the invention provides a use of a rabbit B cell for obtaining an ex vivo B cell culture with a mean doubling time of 20 hours or less. Ex vivo rabbit B cell cultures according to the present invention are typically obtained by expression of Bcl-6, or a rabbit homologue thereof, and an anti-apoptotic nucleic acid molecule in a rabbit B-cell. Further provided is therefore a method for obtaining an ex vivo B cell culture with a mean doubling time of 20 hours or less, the method comprising:
  inducing, enhancing and/or maintaining expression of Bcl-6, or a rabbit homologue thereof, in a B-cell and
  inducing, enhancing and/or maintaining expression of an anti-apoptotic nucleic acid molecule in said B-cell,
characterized in that said B cell is a rabbit B cell.

Preferably, ex vivo rabbit B cell cultures are produced with a mean doubling time of less than 20 hours. More preferably, said mean doubling time is less than 19 hours or even less than 18 hours. A shorter doubling time allows faster and higher antibody production, which enhances the time to—and efficacy of—testing and screening for a desired antibody and isolation and/or identification of antibodies of interest. Moreover, if mAbs need to be developed for an individual patient, the shorter doubling time of rabbit B cells allows for a quicker start of the patient's specific mAb therapy.

A method according to the present invention, using rabbit B cells, thus provides the advantage that antibody can be obtained, tested, identified, isolated and/or produced ex vivo within a shorter time frame as compared to currently known human, murine or llama B cell cultures.

The fact that the present invention provides a B cell culture with a short doubling time provides the advantage that a sufficient quantity of antibody can be obtained within a shorter period of time as compared to existing methods. For instance, in a method as disclosed in WO 2007/067046 a collection of B cells obtained from a human individual is stabilized using Bcl-6 and an anti-apoptotic nucleic acid (or compounds increasing the expression of such nucleic acids) and subsequently cultured. This results in stabilized human B cells, which are capable of both proliferating and producing antibody. During culturing, the stabilized B cells produce antibody, which is secreted into the culture medium. Subsequently, these antibodies are preferably tested for a desired specificity (and/or affinity). For current test procedures, an antibody concentration of at least 100 ng/ml culture medium is typically required. After 15-20 days of culturing stabilized human B cells, such minimal antibody concentration is obtained. Therefore, using human B cell cultures, antibody is harvested at least 15-20 days after starting the culture, typically around day 20. Llama B cells have a similar growth rate as human B cells, so that if a llama B cell culture is used, antibody is also typically harvested at least 15-20 days after starting the culture. With murine B cells, which have a longer doubling time, antibodies with a minimal concentration of 100 ng/ml are typically obtained after more than 20 days.

After testing the antibodies, the corresponding B cells of interest are often selected and isolated for further use. Given the fact that antibody testing normally takes about three days, human or llama B cells of interested are typically selected and isolated after 18-23 days from the start of the B cell culture, whereas murine B cells of interest are typically selected and isolated after more than 23 days. The isolated B cells are then further cultured. A B cell culture with human, llama or murine B cells of interest is thus typically obtained after about three weeks from the start of the B cell culture. With a method according to the present invention, however, an antibody concentration of at least 100 ng/ml is already obtained after 11-12 days. Hence, antibody can now already be harvested 11-12 days after starting the B cell culture, whereas one had to maintain a human (or llama) B cell culture for at least 15-20 days before harvesting antibody. If the testing procedure takes three days, rabbit B cells of interest are thus selected and isolated within 14-15 days from the start of the B cell culture, which is significantly faster as compared to the situation wherein human or murine B cells are cultured. In conclusion, whereas it typically takes about three weeks for obtaining a human, llama or murine B cell culture which produces a sufficient concentration of antibody, with the insight of the present invention a B cell culture with rabbit B cells producing a sufficient Ab concentration is already obtained after two weeks. This is a major advantage over existing methods. One aspect of the invention therefore provides a method for obtaining antibodies, preferably for use in one or more testing assays requiring a minimal antibody concentration of at least 100 ng/ml, the method comprising:

inducing, enhancing and/or maintaining expression of Bcl-6 in a rabbit B-cell;
inducing, enhancing and/or maintaining expression of an anti-apoptotic nucleic acid molecule in said B-cell;
culturing said B cell ex vivo; and
harvesting antibodies produced by said B cell within 10-14 days, preferably within 11-12 days. Said harvested antibodies are preferably tested using one or more assays requiring a minimal antibody concentration of at least 100 ng/ml.

As described above, the obtained antibodies are typically used for testing for a desired specificity and/or affinity. Current test methods often require a minimal antibody concentration of 100 ng/ml, but if more sensitive detection methods are used, the antibodies can be harvested earlier. Whatever the sensitivity of the test method, using rabbit B cells with a method according to the present invention, the required minimal antibody concentration is obtained earlier as compared to the use of currently known human, llama or murine B cells, due to the significant faster doubling time of rabbit B cells. For instance, if a minimal antibody concentration of only 30 ng/ml is required, instead of 100 ng/ml, this concentration is typically reached using human B cells after 13-18 days from the start of the B cell culture, whereas a rabbit B cell culture would only need 9-10 days to obtain this minimal antibody concentration. Thus, again, antibody testing and isolation of B cells of interest can be performed earlier. In practice, the current inventors obtain and test the rabbit antibodies within 7-14 days from the start of a B cell culture. Before the present invention, ex vivo B cell cultures allowing antibody testing at significant earlier stages as compared to ex vivo human B cell cultures were not available. Further provided is therefore a method for obtaining antibodies, the method comprising:

inducing, enhancing and/or maintaining expression of Bcl-6, or a rabbit homologue thereof, in a rabbit B-cell;
inducing, enhancing and/or maintaining expression of an anti-apoptotic nucleic acid molecule in said rabbit B-cell;
culturing said B cell ex vivo; and
harvesting antibodies produced by said B cell within 7-14 days, preferably within 9-12 or 9-10 days. Said harvested antibodies are preferably tested using one or more assays requiring a minimal antibody concentration of about 30 ng/ml.

As used herein, the term "rabbit B cell" means a B cell that has been obtained from a rabbit, or a B cell that originates from a rabbit B cell. An example of B cells originating from a rabbit B cell is the progeny of a rabbit B cell that is formed after one or more cell division cycles. Such progeny for instance includes an ex vivo culture of rabbit B cells.

An ex vivo rabbit B cell culture is a culture that contains rabbit B cells and/or progeny thereof. Other kinds of cells may also be present in the culture. For instance, B cell stimulator cells such as CD40 positive L cells and/or EL4B5 cells are typically also present in a B cell culture according to the invention. Additionally, other kinds of cells, which were also present in a B cell-containing sample, could still be present in a B cell culture. When present in B cell culturing conditions, such non-B cells are typically less capable of proliferating as compared to B cells, so that the number of such contaminating cells will typically decline in time. Preferably, at least 70% of the cells of a rabbit B cell culture are rabbit B cells. More preferably, at least 75%, 80%, 85%, 90% or 95% of the cells of said rabbit B cell culture are rabbit B cells. In a particularly preferred embodiment, rabbit B cells and B cell stimulator cells such as CD40 positive L cells and/or EL4B5 cells are essentially the only kinds of cell present in a rabbit B cell culture.

Preferably, the B cells of a rabbit B cell culture according to the invention are progeny of one original rabbit B cell, so that monoclonal antibodies are produced by the B cell culture.

The term "mean doubling time" is defined herein as the mean time required, starting from a culture with a certain original amount of B cells, to obtain a culture with a number of B cells that is two times said original B cell number. Since not every B cell will proliferate at exactly the same rate, mean values are typically used for a B cell culture as a whole.

Bcl-6 encodes a transcriptional repressor which is required for normal B cell and T cell development and maturation and which is required for the formation of germinal centers. Bcl-6 is highly expressed in germinal center B cells whereas it is hardly expressed in plasma cells. Bcl-6 inhibits differentiation of activated B cells into plasma cells. In a method according to the invention, Bcl-6 expression product, or the expression product of a rabbit homologue thereof, remains present in the rabbit B cells of an ex vivo culture. The presence of Bcl-6, or a rabbit homologue thereof, together with the presence of an anti-apoptotic nucleic acid, prolongs the replicative life span of the B cells. Expression of Bcl-6, or a rabbit homologue thereof, is preferably induced, enhanced or maintained by administering a Bcl-6 expression-promoting compound, or a compound that promotes expression of a rabbit homologue of Bcl-6, to the rabbit B cell(s) used for culturing, or by culturing rabbit B cells in the presence of such compound.

Further provided is therefore a method according to the invention, comprising:
providing said rabbit B cell with a compound capable of directly or indirectly enhancing expression of Bcl-6, or expression, of a rabbit homologue of Bcl-6; and/or
culturing said rabbit B cell in the presence of a compound capable of directly or indirectly enhancing expression of Bcl-6, or expression of a rabbit homologue of Bcl-6.

Various compounds capable of directly or indirectly enhancing expression of Bcl-6, or expression of a rabbit homologue of Bcl-6, are known in the art. Such compound for instance comprises a Signal Transducer of Activation and Transcription 5 (STAT5) protein, or a rabbit homologue thereof, or a functional part or a functional derivative thereof, and/or a nucleic acid sequence coding therefore. STAT5 is a signal transducer capable of enhancing Bcl-6 expression. There are two known forms of STAT5, STAT5a and STAT5b, which are encoded by two different, tandemly linked genes. Administration and/or activation of STAT5, or a rabbit homologue thereof, results in enhanced levels of Bcl-6, or enhanced levels of a rabbit homologue of Bcl-6. Hence, STAT5, or a rabbit homologue thereof, or a functional part or a functional derivative thereof is capable of directly increasing expression of Bcl-6, or expression of a rabbit homologue of Bcl-6. Provided is therefore a method according to the invention comprising providing said rabbit B cell with STAT5, or with a rabbit homologue thereof, or with a functional part or a functional derivative thereof, or providing said rabbit B cell with a nucleic acid molecule encoding STAT5, or a rabbit homologue thereof, or a functional part or a functional derivative thereof, or culturing said rabbit B cell in the presence of STAT5, or in the presence of a rabbit homologue thereof, or a functional part or a functional derivative thereof.

The presence of STAT5, or a rabbit homologue thereof, directly increases the amount of Bcl-6, or the amount of a rabbit homologue of Bcl-6. It is also possible to indirectly increase expression of Bcl-6, or expression of a rabbit homologue thereof. This is for instance done by regulating the amount of a certain compound, which in turn is capable of directly or indirectly activating STAT5, or a rabbit homologue thereof, and/or increasing expression of STAT5, or expression of a rabbit homologue thereof. Hence, in one embodiment the expression and/or activity of endogenous and/or exogenous STAT5, or the expression of a rabbit homologue thereof, is increased. It is for instance possible to indirectly enhance expression of Bcl-6, or expression of a rabbit homologue thereof, by culturing a rabbit B cell in the presence of interleukin (IL) 2 and/or IL4 which are capable of activating STAT5, or activating a rabbit homologue of STAT5, which in turn increases expression of Bcl-6, or expression of a rabbit homologue of Bcl-6.

As used herein, the term "rabbit homologue" of, for instance, Bcl-6 or STAT5 means a rabbit protein corresponding to Bcl-6 or STAT5, which means that it has a corresponding, similar function in rabbit B cells as compared to the function of Bcl-6 or STAT5 in human B cells.

It is, however, preferred to provide a rabbit B cell with a nucleic acid molecule encoding Bcl-6, or encoding a rabbit homologue thereof, or a functional part or a functional derivative thereof. This way, it is possible to directly regulate the concentration of Bcl-6, or the concentration of a rabbit homologue thereof, in said rabbit B cell. Also provided is therefore a method according to the invention comprising providing said rabbit B cell with a nucleic acid molecule encoding Bcl-6, or encoding a rabbit homologue of Bcl-6, or a functional part or a functional derivative thereof. In one embodiment, said nucleic acid molecule is constitutively active, meaning that Bcl-6, or a rabbit homologue thereof, or a functional part or a functional derivative thereof, is continuously expressed, independent of the presence of a regulator. In another embodiment, said nucleic acid molecule is inducible, meaning that the expression thereof is regulated by at least one inducer and/or repressor. This way, expression of said nucleic acid molecule is regulated at will. For instance, Tet-On and Tet-Off expression systems (for example Tet-On® and Tet-Off® Advanced Inducible Gene Expression Systems, Clontech) can be used for inducible expression of a nucleic acid sequence of interest. In these systems expression of the transcriptional activator (tTA) is regulated by the presence (Tet-On) or absence (Tet-Off) of tetracycline (TC) or a derivative like doxycycline (dox). In principle, tTA is composed of the *Escherichia coli* Tet repressor protein (TetR) and the Herpes simplex virus transactivating domain VP16. tTA regulates transcription of a nucleic acid sequence of interest under the control of a tetracycline-responsive element (TRE) comprising the Tet operator (TetO) DNA sequence and a promoter sequence, for instance the human cytomegalovirus (hCMV) promoter. A nucleic acid sequence encoding, for instance, Bcl6, or a rabbit homologue thereof, or a functional part or a functional derivative thereof, can be placed downstream of this promoter.

In the Tet-off system, tTA binds to TRE in the absence of TC or dox and transcription of a nucleic acid sequence of interest is activated, whereas in the presence of TC or dox tTA cannot bind TRE and expression of a nucleic acid sequence of interest is inhibited. In contrast, the Tet-on system uses a reverse tTA (rtTA) that can only bind the TRE in the presence of dox. Transcription of a nucleic acid sequence of interest is inhibited in the absence of dox and activated in the presence of dox.

In another embodiment, inducible expression is executed using a hormone inducible gene expression system such as for instance an ecdysone inducible gene expression system (for example RheoSwitch®, New England Biolabs) (Christopherson, K. S. et al. PNAS 89, 6314-8 (1992)). Ecdysone is an insect steroid hormone from for example *Drosophila melanogaster*. In cells transfected with the ecdysone receptor, a heterodimer consisting of the ecdysone receptor (Ecr) and retinoid X receptor (RXR) is formed in the presence of an ecdyson agonist selected from ecdysone, one of its analogues such as muristerone A and ponasterone A, and a non-steroid ecdysone agonist. In the presence of an agonist, Ecr and RXR interact and bind to an ecdysone response element that is present on an expression cassette. Expression of a nucleic acid sequence of interest that is placed in an expression cassette downstream of the ecdysone response element is thus induced by exposing a rabbit B-cell to an ecdyson agonist.

In yet another embodiment of the invention inducible expression is executed using an arabinose-inducible gene expression system (for example pBAD/gIII kit, Invitrogen) (Guzman, L. M. et al. Bacteriol 177, 4121-4130 (1995)). Arabinose is a monosaccharide containing five carbon atoms. In cells transfected with the arabinose-inducible promoter PBAD expression of a nucleic acid sequence of interest placed downstream of PBAD can then be induced in the presence of arabinose.

It is also possible to use (a nucleic acid molecule encoding) a Bcl-6 protein, or a rabbit homologue thereof, or a functional part or functional derivative thereof, wherein the activity of said Bcl-6 or rabbit homologue or functional part or functional derivative is regulated by at least one inducer and/or repressor. A non-limiting example is a fusion protein wherein a regulatory element is fused to a sequence encoding at least part of Bcl-6 or a rabbit homologue thereof. For instance, an estrogen receptor (ER) is fused to Bcl-6, resulting in fusion protein ER-Bcl-6. This fusion protein is inactive because it forms a complex with heat shock proteins in the cytosol. Upon administration of the exogenous inducer 4 hydroxy-tamoxifen (4HT), the fusion protein ER-Bcl-6 dissociates from the heat shock proteins, so that the Bcl-6 part of the fusion protein becomes active.

As used herein, the term "anti-apoptotic nucleic acid molecule" refers to a nucleic acid molecule, which is capable of delaying and/or preventing apoptosis in a rabbit B cell. Preferably, said anti-apoptotic nucleic acid molecule is capable of delaying and/or preventing apoptosis in a plasmablast-like rabbit B cell, which is capable of both proliferating and producing antibody. Preferably, an anti-apoptotic nucleic acid molecule is used which comprises an exogenous nucleic acid molecule. This means that either a nucleic acid sequence is used which is not naturally expressed in rabbit B cells, or that an additional copy of a naturally occurring nucleic acid sequence is used, so that expression in the resulting rabbit B cells is enhanced as compared to natural rabbit B cells. Various anti-apoptotic nucleic acid molecules are known in the art, so that various embodiments are available. Preferably, an anti-apoptotic nucleic acid molecule is used which is an anti-apoptotic member of the Bcl-2 family because anti-apoptotic Bcl-2 proteins are good apoptosis inhibitors in B cells. Many processes that are controlled by the Bcl-2 family (which family includes both pro- and anti-apoptotic proteins) relate to the mitochondrial pathway of apoptosis. The use of anti-apoptotic Bcl-2 family members Bcl-2, Bcl-xL, Bcl-w, Bcl-2-related protein A1 (also named Bcl2-A1 or A1), Bcl-2 like 10 (Bcl2L10) and Mcl-1, or a rabbit homologue thereof, or a functional part or functional derivative thereof, is preferred because Bcl-2, Bcl-xL, Bcl-w, A1, Bcl2L10 and Mcl-1 are generally integrated with the outer mitochondrial membrane. They directly bind and inhibit the pro-apoptotic proteins that belong to the Bcl-2 family to protect mitochondrial membrane integrity.

A preferred embodiment therefore provides a method according to the invention, wherein said anti-apoptotic nucleic acid molecule comprises an anti-apoptotic gene of the Bcl2 family, preferably Bcl-xL or Mcl-1 or Bcl-2 or A1 or Bcl-w or Bcl2L10, or a rabbit homologue thereof, or a functional part or a functional derivative thereof.

In one embodiment, expression of Bcl-xL or Mcl-1 or Bcl-2 or A1 or Bcl-w or Bcl2L10, or a rabbit homologue thereof, is induced, enhanced or maintained by administering at least one compound, capable of promoting expression of any of these anti-apoptotic genes, to rabbit B cell(s), or by culturing rabbit B cells in the presence of such compound(s). Further provided is therefore a method according to the invention, comprising:
providing said rabbit B cell with a compound capable of directly or indirectly enhancing expression of Bcl-xL and/or Mcl-1 and/or Bcl-2 and/or A1 and/or Bcl-w and/or Bcl2L10, or a rabbit homologue thereof; and/or
culturing said rabbit B cell in the presence of a compound capable of directly or indirectly enhancing expression of Bcl-xL and/or Mcl-1 and/or Bcl-2 and/or A1 and/or Bcl-w and/or Bcl2L10, or a rabbit homologue thereof.

Preferably, however, a rabbit B cell is provided with at least one nucleic acid molecule encoding an anti-apoptotic gene of the Bcl2 family, preferably selected from the group consisting of Bcl-xL, Mcl-1, Bcl-2, A1, Bcl-w, Bcl2L10, and rabbit homologues thereof, and functional parts and functional derivatives thereof. This way, it is possible to directly enhance the amount of expression product in said rabbit B cell. Also provided is therefore a method according to the invention, comprising providing said rabbit B cell with at least one nucleic acid molecule encoding an anti-apoptotic gene of the Bcl2 family, preferably selected from the group consisting of Bcl-xL, Mcl-1, Bcl-2, A1, Bcl-w, Bcl2L10, and rabbit homologues thereof, and functional parts and functional derivatives thereof. In one embodiment, said nucleic acid molecule is constitutively active, meaning that said nucleic acid molecule is continuously expressed. In another embodiment, said nucleic acid molecule is inducible, meaning that the expression thereof is regulated by at least one inducer and/or repressor. Non-limiting examples of inducible nucleic acid expression systems known in the art are described herein before.

In a particularly preferred embodiment said anti-apoptotic nucleic acid molecule encodes Bcl-xL or Mcl-1, or a rabbit homologue thereof, or a functional part or a functional derivative thereof. According to the present invention, a combination of Bcl-6 and Bcl-xL is particularly well capable of increasing the replicative life span of rabbit B-cells, thereby forming long term cultures of the resulting plasmablast-like B-cells. The same holds true for a combination of Bcl-6 and Mcl-1. Most preferably, said anti-apoptotic nucleic acid encodes Bcl-xL or a functional part or a functional derivative thereof.

A functional part of Bcl-6, Bcl-xL, Mcl-1, Bcl-2, A1, Bcl-w or Bcl2L10, or of a rabbit homologue thereof, is a proteinaceous molecule that has the same capability—in kind, not necessarily in amount—of increasing the replicative life span of a rabbit B cell as compared to natural Bcl-6, Bcl-xL, Mcl-1, Bcl-2, A1, Bcl-w or Bcl2L10, or a rabbit homologue thereof, respectively. Such functional part is for instance devoid of amino acids that are not, or only very little, involved in said capability.

For instance, functional parts of Bcl-xL, Mcl-1, Bcl-2, A1, Bcl-w and Bcl2L10, or of a rabbit homologue thereof, are defined herein as fragments of Bcl-xL, Mcl-1, Bcl-2, A1, Bcl-w and Bcl2L10, respectively, or of a rabbit homologue thereof, which have retained the same kind of anti-apoptotic characteristics as full length Bcl-xL, Mcl-1, Bcl-2, A1, Bcl-w and Bcl2L10, respectively, or a rabbit homologue thereof (in kind, but not necessarily in amount). Functional parts of Bcl-xL, Mcl-1, Bcl-2, A1, Bcl-w or Bcl2L10, or of a rabbit homologue thereof, are typically shorter fragments of Bcl-xL, Mcl-1, Bcl-2, A1, Bcl-w or Bcl2L10, respectively, or of a rabbit homologue thereof, which are capable of delaying and/or preventing apoptosis in a rabbit B-cell. Such functional parts are for instance devoid of sequences which do not significantly contribute to the anti-apoptotic activity of Bcl-xL, Mcl-1, Bcl-2, A1, Bcl-w and Bcl2L10. A functional part of Bcl-6, or of a rabbit homologue thereof, is typically a shorter fragment of Bcl-6, or a shorter fragment of a rabbit homologue thereof, which is capable of increasing the replicative life span of a rabbit B cell.

A functional derivative of Bcl-6, Bcl-xL, Mcl-1, Bcl-2, A1, Bcl-w or Bcl2L10, or of a rabbit homologue thereof, is defined as a Bcl-6, Bcl-xL, Mcl-1, Bcl-2, A1, Bcl-w or Bcl2L10 protein, respectively, or a rabbit homologue thereof, which has been altered but has maintained its capability (in kind, not necessarily in amount) of increasing the replicative life span of a rabbit B cell. A functional derivative is provided in many ways, for instance through conservative amino acid substitution wherein one amino acid is substituted by another amino acid with generally similar properties (size, hydrophobicity, etc), such that the overall functioning is not seriously affected. Alternatively, a functional derivative for instance comprises a fusion protein with a detectable label or with an inducible compound.

Another aspect of the present invention solves the problem of efficiently introducing a nucleic acid molecule of interest into rabbit B cells. Contrary to expectations, the inventors found that the commonly used ampho retroviral vector, which is suitable for infecting rodent cells such as murine cells and which was therefore expected to be also capable of transducing rabbit B cells, appeared not to transduce rabbit B cells efficiently; the transduction efficiency of an ampho vector at 4 days after transduction appeared lower than 1% in rabbit B cells. Therefore, the present inventors had to search for other gene delivery vehicles. Surprisingly, the inventors discovered that a gene delivery vehicle which comprises the extracellular domain of a gibbon ape leukemia virus (GALV) envelope protein is capable of transducing rabbit B cells with a high efficiency, typically of 80-90% at 3-5 days after transduction. This property was quite unexpected, since a gibbon ape leukemia virus does not naturally infect rabbits. Rabbit cells were therefore not expected to contain a receptor for a GALV envelope protein; the current finding was mere coincidence. Of note, transduction efficiency of human B cells with a vector containing the extracellular domain of a GALV envelope protein is typically 60-70% at 4 days after transduction, which is often lower than the transduction efficiency of rabbit B cells with this vector, despite the fact that human B cells are primate cells. This is surprising because, since an ape is also a primate, a vector containing a GALV-based envelope protein was expected to be better capable of infecting primate cells as compared to rabbit cells. Of note, murine B cells are indeed not efficiently transduced using a vector that comprises the extracellular domain of a GALV envelope protein, consistent with the fact that a gibbon ape leukemia virus does not infect mice.

Now that the insight of the present invention has been provided that it is possible to efficiently transduce rabbit B cells using at least a functional part of the extracellular domain of a GALV envelope protein, and that the transduction efficiency is even higher than the transduction efficiency of human B cells, new applications have become available. It has now become possible to introduce a nucleic acid molecule of interest into rabbit B cells with high efficiency, which is particularly advantageous for producing an ex vivo rabbit B cell culture according to the present invention. A preferred embodiment of the invention therefore provides a method for increasing the replicative life span of a rabbit B cell, the method comprising:

inducing, enhancing and/or maintaining expression of Bcl-6, or of a rabbit homologue thereof, in a rabbit B-cell and inducing, enhancing and/or maintaining expression of at least one anti-apoptotic nucleic acid in said B-cell, characterized in that said rabbit B cell is provided with a nucleic acid molecule encoding Bcl-6, or encoding a rabbit homologue thereof, or encoding a functional part or a functional derivative thereof, and/or with at least one anti-apoptotic nucleic acid molecule, via transduction with a gene delivery vehicle that comprises the extracellular domain of a gibbon ape leukemia virus (GALV) envelope protein, or at least a functional part of said extracellular domain, or via transduction with a gene delivery vehicle that comprises a protein that has at least 70% sequence identity with the extracellular domain of a GALV envelope protein, or via transduction with a gene delivery vehicle that comprises a protein that has at least 70% sequence identity with at least a functional part of the extracellular domain of a GALV envelope protein. In one preferred embodiment, said extracellular domain is of an envelope protein of GALV strain SEATO. Said extracellular domain preferably comprises SEQ ID NO. 1: MVLLPGSMLLT-SNLHHLRHQMSPGSWKRLIILLSCVFGGGGT-SLQNKNP HQPMTLTWQVLSQTGDVVWDTKAVQPPWTWWPTL KPDVCALAASLES WDIPGTDVSSSKRVRPPDSDYTAAYKQITW-GAIGCSYPRARTRMASSTFY VCPRDGRTLSE-ARRCGGLESLYCKEWDCETTGTGYWL-SKSSKDLITVKW DQNSEWTQKFQQCHQTGWCNPLKIDFTDKGKL-SKDWITGKTWGLRFY VSGHPGVQFTIRLKITNM-PAVAVGPDLVLVEQGPPRTSLALPPPLPPREA PPPSLPDSNSTALATSAQTPTVRK-TIVTLNTPPPTTGDRLFDLVQGAFLTL NATNP-GATESCWLCLAMGPPYYEAIASSGEVAYSTDLDR-CRWGTQGKLT LTEVSGHGLCIGKVPFTHQHLCNQTLSIN-SSGDHQYLLPSNHSWWACST GLTPCLSTSVFNQTRDFCIQVQLIP-RIYYYPEEVLLQAYDNSHPRTKREA VSLT-LAVLLGLGITAGIGTGSTALIKGPIDLQQGLTSLQIAID-ADLRALQDS VSKLEDSLTSLSEVVLQNRRGLDLLFLKEGGLCAAL-KEECCFYIDHSGAV RDSMKKLKEKLDKRQLER-QKSQNWYEGWFNNSPWFTTLL. Preferably, said sequence identity is at least 75%, more preferably at least 80%, more preferably at least 81%, more preferably at least 82%, more preferably at least 83%, more preferably at least 84%, more preferably at least 85%, more preferably at least 86%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%.

As will be understood by the skilled person, said extracellular domain, which is located at the surface (envelope) of a wild type gibbon ape leukemia virus so that it can bind a host cell, is preferably also located at the surface (envelope) of a gene delivery vehicle for transducing rabbit B cells. In one particularly preferred embodiment, a vector or other gene delivery vehicle is used that comprises an envelope protein which contains the extracellular domain and transmembrane domain of a GALV envelope protein, or a functional part thereof, which is fused to the cytoplasmic domain of an ampho envelope protein. This allows particular efficient transduction of rabbit B cells, as shown in the Examples.

As used herein, the term "a functional part of the extracellular domain of a GALV envelope protein" means a part of said extracellular domain which is still capable of binding rabbit B cells, thereby mediating infection and/or transduction of the rabbit B cells. Such functional part may lack one, or multiple, amino acid residues which are not essential for binding, infection and/or transduction of rabbit B cells.

Of course, now that the insight of the present invention has been provided, rabbit B cells can be transduced with any nucleic acid molecule of interest using at least a functional part of the extracellular domain of a GALV envelope protein. Further provided is therefore an isolated or recombinant rabbit B cell bound to the extracellular domain of a GALV envelope protein, or bound to at least a functional part of said extracellular domain, or bound to a protein that has at least 70% sequence identity with at least a functional part of the extracellular domain of a GALV envelope protein. An isolated or recombinant rabbit B cell that is bound via at least a functional part of the extracellular domain of a GALV envelope protein, or via a protein that has at least 70% sequence identity with at least a functional part of the extracellular domain of a GALV envelope protein, to a gene delivery vehicle is also provided herewith. In one preferred embodiment, said extracellular domain is of an envelope protein of GALV strain SEATO. Said extracellular domain preferably comprises SEQ ID NO. 1: MVLLPGSMLLT-SNLHHLRHQMSPGSWKRLIILLSCVFGGGGT-SLQNKNP HQPMTLTWQVLSQTGDVVWDTKAVQPPWTWWPT LKPDVCALAASLES WDIPGTDVSSSKRVRPPDSDYTAAYKQITW-GAIGCSYPRARTRMASSTFY VCPRDGRTLSE-ARRCGGLESLYCKEWDCETTGTGYWL-SKSSKDLITVKW DQNSEWTQKFQQCHQTGWCNPLKIDFTDKGKL-SKDWITGKTWGLRFY VSGHPGVQFTIRLKITNM-PAVAVGPDLVLVEQGPPRTSLALPPPLPPREA PPPSLPDSNSTALATSAQTPTVRK-TIVTLNTPPPTTGDRLFDLVQGAFLTL NATNP-GATESCWLCLAMGPPYYEAIASSGEVAYSTDLDR-CRWGTQGKLT LTEVSGHGLCIGKVPFTHQHLCNQTLSIN-SSGDHQYLLPSNHSWWACST GLTPCLSTSVFNQTRDFCIQVQLIP-RIYYYPEEVLLQAYDNSHPRTKREA VSLT-LAVLLGLGITAGIGTGSTALIKGPIDLQQGLTSLQIAID-ADLRALQDS VSKLEDSLTSLSEVVLQNRRGLDLLFLKEGGLCAAL-KEEECCFYIDHSGAV RDSMKKLKEKLDKRQLER-QKSQNWYEGWFNNSPWFTTLL. Again, said sequence identity is preferably at least 75%, more preferably at least 80%, more preferably at least 81%, more preferably at least 82%, more preferably at least 83%, more preferably at least 84%, more preferably at least 85%, more preferably at least 86%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. Said gene delivery vehicle preferably comprises a nucleic acid molecule of interest, preferably a nucleic acid sequence encoding Bcl-6, or a rabbit homologue thereof, or a functional part or functional derivative thereof, and/or an anti-apoptotic nucleic acid sequence. With such gene delivery vehicle, a stabile rabbit B cell culture according to the present invention can be produced. Said anti-apoptotic nucleic acid sequence is preferably an anti-apoptotic gene of the Bcl2 family, most preferably selected from the group consisting of Bcl-xL, Mcl-1, Bcl-2, A1, Bcl-w, Bcl2L10, and rabbit homologues thereof, and functional parts and functional derivatives thereof.

A use of the extracellular domain of a GALV envelope protein, or at least a functional part thereof that is capable of binding a rabbit B cell, for introducing a nucleic acid molecule of interest into a rabbit B cell is also herewith provided, as well as a use of a protein that has at least 70% sequence identity with at least a functional part of the extracellular domain of a GALV envelope protein for introducing a nucleic acid molecule of interest into a rabbit B cell. Further provided is a use of a gene delivery vehicle comprising at least a functional part of the extracellular domain of a GALV envelope protein, or a gene delivery vehicle comprising a protein that has at least 70% sequence identity with at least a functional part of the extracellular domain of a GALV envelope protein, said gene delivery vehicle further comprising a nucleic acid sequence encoding Bcl-6, or a rabbit homologue thereof, or a functional part or a functional derivative thereof, and at least one anti-apoptotic nucleic acid sequence, for increasing the replicative life span of a rabbit B cell. In one preferred embodiment, said extracellular domain is of an envelope protein of GALV strain SEATO. Said extracellular domain preferably comprises SEQ ID NO. 1:

```
MVLLPGSMLLTSNLHHLRHQMSPGSWKRLIILLSCVFGGGGTSLQNKNPH
QPMTLTWQVLSQTGDVVWDTKAVQPPWTWWPTLKPDVCALAASLESWDIP
GTDVSSSKRVRPPDSDYTAAYKQITWGAIGCSYPRARTRMASSTFYVCPR
DGRTLSEARRCGGLESLYCKEWDCETTGTGYWLSKSSKDLITVKWDQNSE
WTQKFQQCHQTGWCNPLKIDFTDKGKLSKDWITGKTWGLRFYVSGHPGVQ
FTIRLKITNMPAVAVGPDLVLVEQGPPRTSLALPPPLPPREAPPPSLPDS
NSTALATSAQTPTVRKTIVTLNTPPPTTGDRLFDLVQGAFLTLNATNPGA
TESCWLCLAMGPPYYEAIASSGEVAYSTDLDRCRWGTQGKLTLTEVSGHG
LCIGKVPFTHQHLCNQTLSINSSGDHQYLLPSNHSWWACSTGLTPCLSTS
VFNQTRDFCIQVQLIPRIYYYPEEVLLQAYDNSHPRTKREAVSLTLAVLL
GLGITAGIGTGSTALIKGPIDLQQGLTSLQIAIDADLRALQDSVSKLEDS
LTSLSEVVLQNRRGLDLLFLKEGGLCAALKEECCFYIDHSGAVRDSMKKL
KEKLDKRQLERQKSQNWYEGWFNNSPWFTTLL.
```

A preferred chimeric envelope protein, which is also used in the Examples, is shown in FIG. 9. This chimeric envelope protein contains the extracellular domain of a GALV envelope protein (SEQ ID NO. 1): MVLLPGSMLLT-SNLHHLRHQMSPGSWKRLIILLSCVFGGGGT-SLQNKNP HQPMTLTWQVLSQTGDVVWDTKAVQPPWTWWPTL KPDVCALAASLES WDIPGTDVSSSKRVRPPDSDYTAAYKQITW-GAIGCSYPRARTRMASSTFY VCPRDGRTLSE-ARRCGGLESLYCKEWDCETTGTGYWL-SKSSKDLITVKW DQNSEWTQKFQQCHQTGWCNPLKIDFTDKGKL-SKDWITGKTWGLRFY VSGHPGVQFTIRLKITNM-PAVAVGPDLVLVEQGPPRTSLALPPPLPPREA PPPSLPDSNSTALATSAQTPTVRK-TIVTLNTPPPTTGDRLFDLVQGAFLTL NATNP-GATESCWLCLAMGPPYYEAIASSGEVAYSTDLDR-CRWGTQGKLT LTEVSGHGLCIGKVPFTHQHLCNQTLSIN-SSGDHQYLLPSNHSWWACST GLTPCLSTSVFNQTRDFCIQVQLIP-RIYYYPEEVLLQAYDNSHPRTKREA VSLT-LAVLLGLGITAGIGTGSTALIKGPIDLQQGLTSLQIAID-ADLRALQDS VSKLEDSLTSLSEVVLQNRRGLDLLFLKEGGLCAAL-KEEECCFYIDHSGAV RDSMKKLKEKLDKRQLER- QKSQNWYEGWFNNSPWFTTLL, indicated in bold in FIG. 9) and the transmembrane domain of a GALV envelope protein (SEQ ID NO. 2) STIAGPLLLLLLLLILGPCII, indicated underlined in FIG. 9), fused to the cytoplasmic domain of an ampho envelope protein (NRLVQFVKDRISVVQALVLTQQYHQLKPIEYEP see (SEQ ID NO. 3), indicated in italics and dotted-underlined in FIG. 9). A vector or other gene delivery vehicle that comprises this preferred chimeric envelope protein is particularly well capable of introducing a nucleic acid molecule of interest into rabbit B cells.

Further provided is therefore an isolated or recombinant rabbit B cell bound to a chimeric envelope protein as depicted in FIG. 9, or to a protein comprising a chimeric envelope protein as depicted in FIG. 9 or to a protein that has at least 70% sequence identity with a chimeric envelope protein as depicted in FIG. 9. An isolated or recombinant rabbit B cell that is bound via a chimeric envelope protein as depicted in FIG. 9, or via a protein comprising a chimeric envelope protein as depicted in FIG. 9 or via a protein that has at least 70% sequence identity with a chimeric envelope protein as depicted in FIG. 9, to a vector or other gene delivery vehicle is also provided herewith.

Such vector or other gene delivery vehicle is particularly suitable for transducing rabbit B cells with a nucleic acid molecule of interest. Further provided is therefore a use of a chimeric envelope protein as depicted in FIG. 9, or a protein comprising a chimeric envelope protein as depicted in FIG. 9 or a protein that has at least 70% sequence identity with a chimeric envelope protein as depicted in FIG. 9, for introducing a nucleic acid molecule of interest into a rabbit B cell.

Such vector or other gene delivery vehicle is particularly suitable for increasing the replicative life span of rabbit B cells. Further provided is therefore a method for increasing the replicative life span of a rabbit B cell, the method comprising:

inducing, enhancing and/or maintaining expression of Bcl-6, or of a rabbit homologue thereof, in a rabbit B-cell and inducing, enhancing and/or maintaining expression of at least one anti-apoptotic nucleic acid in said B-cell, characterized in that said rabbit B cell is provided with a nucleic acid molecule encoding Bcl-6, or encoding a rabbit homologue thereof, or encoding a functional part or a functional derivative thereof, and/or with at least one anti-apoptotic nucleic acid molecule, via transduction with a vector or other gene delivery vehicle that comprises a chimeric envelope protein as depicted in FIG. 9, or a protein comprising a chimeric envelope protein as depicted in FIG. 9, or a protein that has at least 70% sequence identity with a chimeric envelope protein as depicted in FIG. 9.

Also provided is a use of a gene delivery vehicle comprising a chimeric envelope protein as depicted in FIG. 9, or a protein comprising a chimeric envelope protein as depicted in FIG. 9, or a protein that has at least 70% sequence identity with a chimeric envelope protein as depicted in FIG. 9, said gene delivery vehicle further comprising a nucleic acid sequence encoding Bcl-6, or a rabbit homologue thereof, or a functional part or a functional derivative thereof, and at least one anti-apoptotic nucleic acid sequence, for increasing the replicative life span of a rabbit B cell.

It is emphasized that, although a GALV-based gene delivery vehicle is very suitable for efficient transduction of rabbit B cells with one or more nucleic acid molecule(s) of interest, such as Bcl-6 and an anti-apoptotic nucleic acid molecule, the use of a GALV-based gene delivery vehicle is not mandatory for obtaining rabbit B cells with a short doubling time of 20 hours or less. Other gene delivery vehicles can also be used for introducing Bcl-6 and an anti-apoptotic nucleic acid molecule into rabbit B cells (although the efficiency will often be lower), in order to produce rabbit B cells with a doubling time of 20 hours or less. As long as Bcl-6 and an anti-apoptotic nucleic acid molecule are introduced into rabbit B cells, a fast-growing B cell culture can be obtained, although it may take longer for the lower amount of originally transduced rabbit B cells to grow out. An advantage of the use of a gene delivery vehicle that is able to efficiently transduce rabbit B cells, such as a GALV-based gene delivery vehicle as described herein, is that a higher proportion of the originally isolated B cells will be transduced, so that B cells derived therefrom will be present in the resulting B cell culture. This results in a higher diversity of B cells within the B cell culture as compared to a situation wherein a gene delivery vehicle with a lower transduction efficiency is used, because in the latter case a lower proportion of the original B cells are transduced. The presence of a higher diversity of B cells within the resulting B cell culture improves the chance of isolating one or more B cells with a desired property. Hence, in principle, the higher the transduction efficiency of the gene delivery vehicle, the higher the diversity of B cells within the resulting B cell culture.

In order to induce expression in rabbit B cells, a nucleic acid molecule of interest is preferably operably linked to a promoter. Non-limiting examples include a CMV promoter and a CAG promoter. In one aspect, such promoter is inducible, meaning that its activity is influenced by at least one compound, such as for instance a transcription factor.

As used herein, the term "gene delivery vehicle" means any compound capable of transferring a nucleic acid molecule into a host cell. Non-limiting examples of gene delivery vehicles include (viral) vectors and plasmids. The term "gene delivery vehicle comprising at least a functional part of the extracellular domain of a GALV envelope protein" means a gene delivery vehicle comprising at least part of the extracellular domain of a GALV envelope protein, wherein said extracellular domain, or said part thereof, is capable of binding a rabbit B cell so that nucleic acid can be introduced into said rabbit B cell. As described herein before, said extracellular domain, or part thereof, is preferably located at the surface of the gene delivery vehicle, so that it can bind a receptor on a rabbit B cell. Likewise, if a gene delivery vehicle according to the invention comprises a protein that has at least 70% sequence identity with at least a functional part of the extracellular domain of a GALV envelope protein, said protein is preferably located at the surface of the gene delivery vehicle, so that it can bind a receptor on a rabbit B cell.

The percentage of identity of an amino acid or nucleic acid sequence, or the term "% sequence identity", is defined herein as the percentage of residues in a candidate amino acid or nucleic acid sequence that is identical with the residues in a reference sequence after aligning the two sequences and introducing gaps, if necessary, to achieve the maximum percent identity. Methods and computer programs for the alignment are well known in the art, for example "Align 2".

A GALV envelope protein is a protein that is naturally present in the viral envelope of gibbon ape leukemia virus and that is involved in infection of host cells. The target specificity is typically determined by the envelope protein. In one embodiment, said envelope protein is of GALV strain SEATO. Retroviral vectors containing the GALV envelope protein are known in the art and can be produced using procedures that are commonly used in the art of molecular biology, see for instance Lam et al., 1996.

The term "operably linked to a promoter" means that a nucleic acid sequence of interest is located sufficiently close to a promoter so that the promoter can influence expression thereof. Typically, such promoter will induce or increase expression of said nucleic acid of interest. The term "expression activity" refers to such induction or enhancement of expression.

As mentioned herein before, the present invention provides the insight that an ex vivo rabbit B cell culture can be obtained with a shorter mean doubling time as compared to currently known human or murine B cell cultures. This is all the more surprising because non-rabbit compounds, such as a human Bcl-6 nucleic acid sequence, murine IL21 and human CD40L, were used in the current Examples. As shown in the Examples, the present inventors transduced rabbit B cells with a nucleic acid molecule containing a human Bcl-6 sequence and a human Bcl-xL or Mcl-1 sequence. Even though human sequences were used, and the rabbit cells were cultured in the presence of murine IL21 and human CD40L, the rabbit B cells surprisingly appeared to proliferate faster and to produce more antibody as compared to human and murine B cells.

Hence, according to the invention, rabbit B cells proliferate very well using human and murine compounds. Under these reaction conditions, the rabbit B cells even proliferate better than human and murine B cells. This has amongst other things the advantage that currently used reaction conditions for human B cells do not have to be adjusted for rabbit B cells. There is no need to obtain rabbit IL21, rabbit CD40 or rabbit nucleic acid sequences encoding Bcl-6 or an anti-apoptotic gene. Instead, currently available human or murine compounds can be used. One aspect of the invention therefore provides a method for increasing the replicative life span of a rabbit B cell, the method comprising:
inducing, enhancing and/or maintaining expression of Bcl-6, or a rabbit homologue thereof, in a rabbit B-cell and
inducing, enhancing and/or maintaining expression of an anti-apoptotic nucleic acid molecule in said B-cell, characterized in that said rabbit B cell is provided with at least one nucleic acid molecule selected from the group consisting of:
a nucleic acid molecule encoding a non-rabbit Bcl-6 or a functional part or a functional derivative thereof; and
a non-rabbit anti-apoptotic nucleic acid molecule.

Preferably, said non-rabbit nucleic acid molecule is a human nucleic acid molecule because human Bcl-6 and human anti-apoptotic sequences appear to provide particularly good results in rabbit B cells. In a particularly preferred embodiment, a rabbit B cell is provided with a nucleic acid molecule encoding human Bcl-6 and with a human anti-apoptotic nucleic acid molecule, preferably human Bcl-xL or human Mcl-1 or human Bcl-2 or human A1 or human Bcl-w or human Bcl2L10.

Furthermore, a method according to the invention is provided, further comprising providing said rabbit B cell with IL21 and CD40L. Preferably, non-rabbit IL21 and/or non-rabbit CD40L is used. Preferably, said IL21 is murine or human IL21, most preferably murine IL21. In another preferred embodiment, said CD40L is murine or human CD40L, most preferably human CD40L.

Besides increasing Bcl-6 expression and the expression of an anti-apoptotic nucleic acid molecule, it is also advantageous to induce, enhance and/or maintain expression of Blimp-1, or a rabbit homologue thereof, in a rabbit B-cell. This enhances antibody production of said B cell. One aspect thus provides a method according to the invention, wherein the method further comprises inducing, enhancing and/or maintaining expression of Blimp-1, or a rabbit homologue thereof, in said rabbit B-cell.

The extent of expression of Blimp-1, or of a rabbit homologue thereof, in a rabbit B cell is regulated in a variety of ways. In one embodiment a rabbit B cell is provided with a compound, which is capable of directly or indirectly increasing expression of Blimp-1, or expression of a rabbit homologue thereof. Additionally, or alternatively, a rabbit B cell is cultured in the presence of a compound capable of directly or indirectly increasing expression of Blimp-1, or expression of a rabbit homologue thereof. Further provided is therefore a method according to the invention, further comprising:
providing said rabbit B cell with a compound capable of directly or indirectly increasing expression of Blimp-1, or expression of a rabbit homologue thereof; and/or
culturing said rabbit B cell in the presence of a compound capable of directly or indirectly increasing expression of Blimp-1, or expression of a rabbit homologue thereof.

Said compound capable of increasing expression of Blimp-1, or of a rabbit homologue thereof, most preferably comprises IL21. Hence, in one preferred embodiment of the present invention, rabbit B cells are cultured in the presence of IL21, at least during part of the culture time.

In another embodiment said compound capable of increasing Blimp-1 expression comprises a Signal Transducer of Activation and Transcription 3 (STAT3) protein or a functional part or a functional derivative thereof, and/or a nucleic acid molecule coding therefore. STAT3 is a signal transducer, which is involved in B cell development and differentiation. STAT3 is capable of upregulating Blimp-1 expression. In one preferred embodiment, a rabbit B cell is provided with a nucleic acid molecule encoding STAT3 or a functional part or a functional derivative thereof, wherein the expression of said nucleic acid molecule is regulated by an exogenous inducer of repressor, so that the extent of STAT3 expression is regulated at will. For instance, one of the earlier mentioned inducible expression systems is used. In one embodiment a fusion product comprising STAT3, or a functional part or a functional derivative, and ER is used. For instance, a rabbit B cell is provided with a nucleic acid molecule encoding an estrogen receptor (ER) and STAT3 as a fusion protein ER-STAT3. This fusion protein is inactive because it forms a complex with heat shock proteins in the cytosol. This way, STAT3 is unable to reach the nucleus and Blimp-1 expression is not enhanced. Upon administration of the exogenous inducer 4 hydroxy-tamoxifen (4HT), the fusion protein ER-STAT3 dissociates from the heat shock proteins, so that STAT3 is capable of entering the nucleus and activating Blimp-1 expression.

As used herein, a functional part of STAT3 is defined as a fragment of STAT3 that has the same capability—in kind, not necessarily in amount—of increasing expression of Blimp-1, or of a rabbit homologue thereof, as compared to natural STAT3. Such functional part is for instance devoid of amino acids that are not, or only very little, involved in said capability.

A functional derivative of STAT3 is defined as a STAT3 protein, which has been altered but has maintained its capability (in kind, not necessarily in amount) of increasing expression of Blimp-1, or of a rabbit homologue thereof. A functional derivative is provided in many ways, for instance through conservative amino acid substitution wherein one amino acid is substituted by another amino acid with generally similar properties (size, hydrophobicity, etc), such that the overall functioning is not seriously affected. Alternatively, a functional derivative for instance comprises a fusion protein with a detectable label or with an inducible compound.

Since STAT3 is capable of increasing expression of Blimp-1, or increasing expression of a rabbit homologue thereof, it is also possible to indirectly increase expression of Blimp-1, or of a rabbit homologue thereof, by administering a compound capable of increasing the activity and/or expression of STAT3. In one embodiment, a rabbit B cell is therefore provided with a compound that is capable of enhancing the activity of STAT3, so that expression of Blimp-1, or of a rabbit homologue thereof, is indirectly enhanced.

STAT3 is activated in a variety of ways. Preferably, STAT3 is activated by providing a rabbit B cell with a cytokine. Cytokines, being naturally involved in B cell differentiation, are very effective in regulating STAT proteins. Very effective activators of STAT3 are IL21 and IL6, but also IL2, IL7, IL10, IL15 and IL27 are known to activate STAT3. Moreover, Toll-like receptors (TLRs), which are involved in innate immunity, are also capable of activating STAT3. One embodiment therefore provides a method of the invention, wherein said rabbit B cell is cultured in the presence of IL21, IL2, IL6, IL7, IL10, IL15 and/or IL27. Most preferably IL21 is used, since IL21 is particularly suitable for enhancing antibody production of rabbit B cell cultures according to the present invention. IL21 is capable of upregulating Blimp-1 expression, even when Blimp-1 expression is counteracted by BCL6.

Additionally, or alternatively a mutated Janus kinase (JAK), or a mutated rabbit homologue of a JAK, is used in order to activate STAT3. Naturally, a JAK is capable of phosphorylating STAT3 after it has itself been activated by at least one cytokine. A mutated Janus kinase, or a mutated rabbit homologue of a JAK, capable of activating STAT3 independently of the presence of cytokines, is particularly suitable in a method according to the present invention.

In yet another embodiment, expression of Blimp-1, or of a rabbit homologue thereof, is increased by providing a rabbit B cell with a suppressor of cytokine signalling (SOCS) protein, or a rabbit homologue thereof, and/or by activating a SOCS protein or a rabbit homologue thereof within said cell. Alternatively, or additionally, at least one of the E-proteins E47, E12, E2-2 and HEB is used in order to increase expression of Blimp-1, or of a rabbit homologue thereof. E47 is a transcription factor that belongs to a family of helix-loop-helix proteins, named E-proteins. There are four E-proteins, E12, E47, E2-2 and HEB, which are involved in lymphocyte development. E12 and E47 are encoded by one gene, named E2A, which is spliced differently. E proteins have been described as tumor suppressors. One of the specific targets of E47 are the Socs1 and Socs3 genes.

One aspect thus provides a method according to the present invention, further increasing expression of Blimp-1, or of a rabbit homologue thereof, in a rabbit B cell by providing said B cell with a compound capable of directly or indirectly increasing expression of Blimp-1, or of a rabbit homologue thereof, and/or culturing said B cell in the presence of a compound capable of directly or indirectly increasing expression of Blimp-1, or of a rabbit homologue thereof, wherein said compound comprises:

STAT3 or a functional part or a functional derivative thereof, and/or
a compound capable of activating STAT3, and/or
a compound capable of enhancing expression of STAT3, and/or
IL21, IL2, IL6, IL7, IL10, IL15, IL27, a SOCS protein, one of the E-proteins E47, E12, E2-2 or HEB, a mutated Janus kinase and/or a nucleic acid sequence encoding STAT3, or a rabbit homologue or a functional part or a functional derivative thereof.

Most preferably, said compound is IL21.

The invention further provides isolated or recombinant rabbit B cells obtainable with a method according to the presence invention. Such isolated or recombinant rabbit B cells preferably comprise an exogenous anti-apoptotic nucleic acid sequence and an exogenous nucleic acid sequence encoding Bcl-6, or a rabbit homologue thereof, or a functional part or a functional derivative thereof. Further provided is therefore an isolated or recombinant rabbit B cell, comprising an exogenous nucleic acid sequence encoding Bcl-6, or a rabbit homologue thereof, or a functional part or a functional derivative thereof, and an exogenous anti-apoptotic nucleic acid sequence. As explained before, said exogenous nucleic acid molecule either contains a nucleic acid sequence that does not naturally occur in rabbit B cells, or an additional copy of a natural rabbit B cell nucleic acid sequence. Bcl-xL, Mcl-1, Bcl-2, A1, Bcl-w and Bcl2L10, and rabbit homologues thereof, are preferred anti-apoptotic nucleic acid molecules. One preferred aspect therefore provides an isolated or recombinant rabbit B cell, which comprises an exogenous nucleic acid sequence encoding Bcl-6, or a rabbit homologue thereof, or a functional part or a functional derivative thereof, and an exogenous nucleic acid sequence encoding Bcl-xL or Mcl-1 or Bcl-2 or A1 or Bcl-w or Bcl2L10, or a rabbit homologue thereof, or a functional part or a functional derivative thereof.

Said nucleic acid sequence encoding Bcl-6, or a rabbit homologue thereof, or a functional part or a functional derivative thereof, and said exogenous anti-apoptotic nucleic acid sequence may be present on one nucleic acid molecule. Alternatively, these sequences are present on at least two different nucleic acid molecules.

Preferably, non-rabbit sequences are used, as explained before. A preferred embodiment therefore provides an isolated or recombinant rabbit B cell comprising a non-rabbit anti-apoptotic nucleic acid sequence and a non-rabbit nucleic acid sequence encoding Bcl-6, or a rabbit homologue thereof, or a functional part or a functional derivative thereof. Said non-rabbit nucleic acid sequence preferably contain human sequences.

In a particularly preferred embodiment, an isolated or recombinant rabbit B cell is provided which comprises:
a nucleic acid sequence encoding human Bcl-6 or a functional part or a functional derivative thereof, and
a human anti-apoptotic nucleic acid sequence, preferably encoding human Bcl-xL or human Mcl-1 or human Bcl-2 or human A1 or human Bcl-w or human Bcl2L10, or a functional part or a functional derivative thereof. Again, said nucleic acid sequence encoding Bcl-6 or a functional part or a functional derivative thereof, and said anti-apoptotic nucleic acid sequence, may be present on one nucleic acid molecule, or, alternatively, these sequences may be present on at least two different nucleic acid molecules.

The invention also provides ex vivo rabbit B cell cultures obtainable by the methods according to the present invention. An important advantage is the fact that ex vivo B cell cultures are now obtained with a short mean doubling time. Provided is therefore an ex vivo rabbit B cell culture which has a mean doubling time of 20 hours or less. A further preferred embodiment provides an ex vivo rabbit B cell culture comprising rabbit B cells according to the invention. Said rabbit B cells preferably comprise a nucleic acid sequence encoding human Bcl-6 or a functional part or a functional derivative thereof, and an anti-apoptotic nucleic acid sequence. Also provided is an ex vivo rabbit B cell culture comprising rabbit B cells in the presence of non-rabbit IL21 and/or non-rabbit CD40L. Preferably, said IL21 is murine or human IL21, most preferably murine IL21. In another preferred embodiment, said CD40L is murine or human CD40L, most preferably human CD40L.

An antibody when obtained by a method according to the invention is also provided herewith, as well as an antibody produced by a rabbit B cell according to the invention or by an ex vivo rabbit B cell culture according to the invention. Such antibody is particularly useful for therapeutic or diagnostic applications. Preferably, said antibody is a monoclonal antibody.

The invention is further explained in the following examples. These examples do not limit the scope of the invention, but merely serve to clarify the invention.

EXAMPLES

Example 1

Transduction of B Cells

Gene transfer into lymphocytes by traditional methods like calcium phosphate precipitation, liposome formation or electroporation is inefficient but more importantly stable gene integration is generally absent. Viral transduction however leads directly to stable gene integration into the genome of the target cell and can be very efficient if the proper virus envelope is chosen. Both retroviral and lentiviral transductions are suitable for efficient gene transfer. While retroviral integration is dependent on cell division, lentiviral transduction can also be applied to non-dividing cells like plasma B cells. Large-scale preparation of recombinant retrovirus can easily be achieved by using stable producer cell lines such as the Phoenix expression platform (Kinsella and Nolan, 1996). Production of high titer lentivirus tends to be more cumbersome mainly because of the toxicity of the expressed virus proteins and envelopes.

For the current Examples, we used a Moloney Murine Leukemia Virus (MMLV) based platform, using either amphotropic or Gibbon Ape Leukemia Virus (GALV) envelope expressing producer cells (Wilson et al., 1995). In our GALV-based vector, the transmembrane domain of the GALV strain SEATO envelope protein was fused to the cytoplasmic domain of an ampho envelope protein (FIG. 9).

The transfer vector is set-up such that Bcl-6, Bcl-xL and the green fluorescent protein (GFP) marker protein are simultaneously translated from the same viral RNA (FIG. 8). This multicistronic approach is achieved by placing a 'self-cleaving' 2A peptide sequence (Szymczak et al., 2004) between the BCL-6 and BCL-xL coding regions and an Internal Ribosomal Entry Sequence (IRES) upstream of the GFP reporter gene. Viral transduction efficiencies are high and unbiased.

Generation of Immortalized Rabbit B Cells

Human memory B cells were immortalized using the BCL-6/Bcl-xL technology described by Kwakkenbos et al., 2010 and patent application WO 2007/067046. In brief, PBMC's from rabbit blood were isolated using a ficoll density gradient and stained for Ig expression using an antibody that recognizes Ig (IgG H+L: IgG heavy chain and kappa and lambda light chains) sometimes in combination with an IgM specific antibody. B cells were isolated (Ig positive, or Ig positive+IgM negative) using a FACS sorter and stimulated on γ irradiated (50 Gy) mouse L cell fibroblasts stably expressing CD40L (CD40L-L cells, $10^5$ cells $ml^{-1}$) together with recombinant mouse interleukin (IL)-21 for 36-48 hours. Cells were harvested and washed with medium without FCS and cells were then transferred to Retronectin® (Takara, Shiga, Japan)-coated tissue culture plates where they were transduced with a retroviral vector containing BCL-6, Bcl-xL, and GFP as a reporter protein. Alternatively cells were transduced with a retroviral vector containing BCL-6, Mcl-1 and GFP. Transduced B cells were maintained in culture with CD40 Ligand expressing L-cells and IL-21. In FIG. 1 the transduction efficiency is compared for GALV and amphotropic type retroviruses at 4 days after transduction. Four days after transduction with the amphotropic type retrovirus 0.8% of the cells was transduced compared to 80% of cells after transduction with a GALV type retrovirus. Clearly the GALV type retrovirus is superior to the amphotropic type retrovirus for transducing rabbit B cells.

Example 2

Cell Culture.

We maintained B cells ($2\times10^5$ cells $ml^{-1}$) in Iscove's modified Dulbecco's medium (Gibco) containing 8% FBS and penicillin-streptomycin (Roche) supplemented with recombinant mouse interleukin 21 (IL-21) (50 ng $ml^{-1}$) and cultured them on γ irradiated (50 Gy) mouse L cell fibroblasts stably expressing CD40L (CD40L-L cells, 10 cells $ml^{-1}$). To determine cell doubling time cells were cultured in 24-well plates at 50-100.000 cells/well together with CD40L-L cells and IL-21. Every 3-4 days cell were counted and 50-100.000 cells transferred to a new well. In FIG. 2 growth curves are depicted for B cells from two human donors (89 and 93), one llama B-cell sample (Llama) and one rabbit B-cell sample which was transduced with a GALV type retrovirus carrying a nucleic acid molecule containing a human Bcl-6 sequence and a human Bcl-xL (Rb 6XL). Also a growth curve is depicted for one rabbit sample that was transduced with a GALV type retrovirus carrying a nucleic acid molecule containing a human Bcl-6 sequence and a human Mcl-1 (Rb 6M). The transduced rabbit B cells have an average doubling time of 19 hours and thus grow faster than the human or llama B cells that have doubling times between 26 and 32 hours. These average doubling times were originally calculated by determining the increase of B cells during several 3-4 days time intervals, and averaging the obtained results. Subsequently, the overall average doubling time during the whole culturing period was calculated. This resulted in an average doubling time of the transduced rabbit B cells of 18 hours, an average doubling time of the transduced human B cells of 25-29 hours and an average doubling time of the transduced llama B cells of 27 hours. This confirms our observations that our methods yield rabbit B-cell cultures with a mean doubling time of 20 hours or less, whereas human, murine and llama B cells typically have a doubling time of between 25 and 36 hours.

Example 3

B-Cell Receptor Expression and Antigen-Specific Staining

Immortalized human B cells express the B-cell receptor. This quality enables antigen-specific staining and sorting of B cells. To determine whether the B-cell receptor is also expressed on transduced rabbit B cells, B-cell clones are stained with fluorescently labeled antibodies reacting specifically with either rabbit IgG, rabbit IgM or rabbit IgA. B cells were washed in cold (4° C.) cell culture medium and incubated on ice in the dark with cell culture medium containing immunofluorescently labelled antibodies that are specific for either rabbit IgG, IgM, IgA or labelled antigen. Afterwards excess of labelled antibodies or antigen was washed away and B-cell receptor expression analysed on a FACS analyser; the Guava easycyte (Millipore) or FACS Aria3 (BD).

In FIG. 3 three different B-cell clones of different isotypes were stained with fluorescently labelled antibodies specifically recognizing rabbit antibody isotype IgG, IgA or IgM. Clearly the B-cell receptor can be efficiently stained for the different rabbit antibody isotypes. We therefore conclude that immortalized rabbit B cells also express the B-cell receptor.

In addition, also fluorescently labeled influenza proteins were used to stain for influenza-specific B-cells from rabbits that had been immunized with a human influenza vaccine or untreated control rabbits (FIG. 4). Rabbit B cells were stained with fluorescently labeled H1, H3 or influenza B and sorted 1 cell per well using a FACS sorter.

Example 4

Development of Single-Cell Derived, Clonal Rabbit B Cell Cultures.

Transduced B cells were sorted one cell per well using a FACS sorter and cultured in the presence of γ irradiated (50 Gy) mouse L cell fibroblasts stably expressing CD40L (CD40L-L cells, 105 cells ml$^{-1}$) together with recombinant mouse IL-21. Every 3-4 days fresh CD40L-L cells and IL-21 were added. Starting 9 days after seeding the cells (one cell per well), the supernatants were analyzed in ELISA for the production of rabbit immunoglobulin G (IgG). For comparison also the human IgG in the supernatant of human B-cell clones was analyzed in parallel.

In FIG. 7 the antibody concentration in the supernatant is depicted over time starting at 9 days after the initiation of the single cell cultures. The antibody concentration was determined for two human donors and one rabbit B-cell sample that were transduced with a GALV type retrovirus carrying a nucleic acid molecule containing a human Bcl-6 sequence and a human Bcl-xL and for one rabbit B-cell sample that was transduced with a GALV type retrovirus carrying a nucleic acid molecule containing a human Bcl-6 sequence and a human Mcl-1. B cell clones from rabbits produce IgG concentrations of 30 ng/ml and 100 ng/ml within a shorter time period (9-10 days and 11-12 days, respectively) than do the human B-cell clones (13-18 and 15-20 days, respectively). This provides the important advantage that it allows for earlier screening for antibodies of interest of rabbit B cell clones, compared to human B cell clones.

Example 5

Immunization of Rabbits.

2 New Zealand White rabbits were immunized with a human influenza vaccine containing 15 ug H1N1, 15 ug H3N2 and 15 ug infl B in complete Freunds adjuvans. After 3 weeks rabbits were boosted with the same vaccine in incomplete Freunds adjuvans. Five days after the boost rabbits were bled, B-cells were isolated from the blood and transduced with a GALV type retrovirus (containing the extracellular domain and transmembrane domain of the GALV strain SEATO envelope protein, fused to the cytoplasmic domain of an ampho envelope protein) carrying a nucleic acid molecule containing a human Bcl-6 sequence and a human Bcl-xL. Transduced B cells were seeded at different cell densities into culture plates and cultured as described in Example 4. Also, transduced B cells were labeled with fluorescently labeled components of the vaccine; H1, H3 or influenza B and sorted 1 cell per well using a FACS sorter and cultured as described in Example 4. The supernatants of the cultured cells were analyzed for binding to the complete vaccine or to its individual components. The results are depicted in FIGS. 4-6 and show that antigen-specific B cells can be identified in the B-cell pool from vaccinated rabbits by seeding cells at different density (FIG. 5) and also very efficiently by sorting cells using the labeled antigens (FIG. 4 and FIG. 6).

Example 6

Rabbit B Cells are Immortalized by the Introduction of the Genes Bcl-6 and Bcl-xl Using an Amphotropic Type Retrovirus.

Immortalization of rabbit B cells by introduction of the genes Bcl-6 and Bcl-xl can be achieved by using different types of vectors, such as for instance GALV and amphotrophic type retroviruses as is shown in Example 1. The growth of B cells transduced with the amphotrophic type retrovirus was further pursued to confirm that introduction of Bcl-6 and Bcl-xl by amphotrophic retrovirus also leads to immortalization of rabbit B cells. Four days after transduction with the amphotropic type retrovirus 0.8% of the cells was transduced compared to 80% of cells after transduction with a GALV type retrovirus (FIG. 1 and FIG. 10). Ten days after transduction 94% of the cell population transduced with the amphotrophic retrovirus was GFP positive demonstrating that the transduced cells overgrow the non-transduced cells (FIG. 10).

To determine cell doubling time cells were cultured as done in Example 2 in 24-well plates at 50-100.000 cells/well together with CD40L-L cells and IL-21. Every 3-4 days cell were counted and 50-100.000 cells transferred to a new well. In FIG. 11 the growth curve is depicted for rabbit B cells transduced with amphotrophic virus. The calculated doubling time is 19 hours, which is comparable to rabbit B cells transduced with GALV type retrovirus (18 hours). In conclusion, introduction of Bcl-6 and Bcl-xl into rabbit B cells by amphotrophic retrovirus also results in immortalization of rabbit B cells, although the transduction efficiency is much lower as compared to a GALV based vector.

Figure 1:
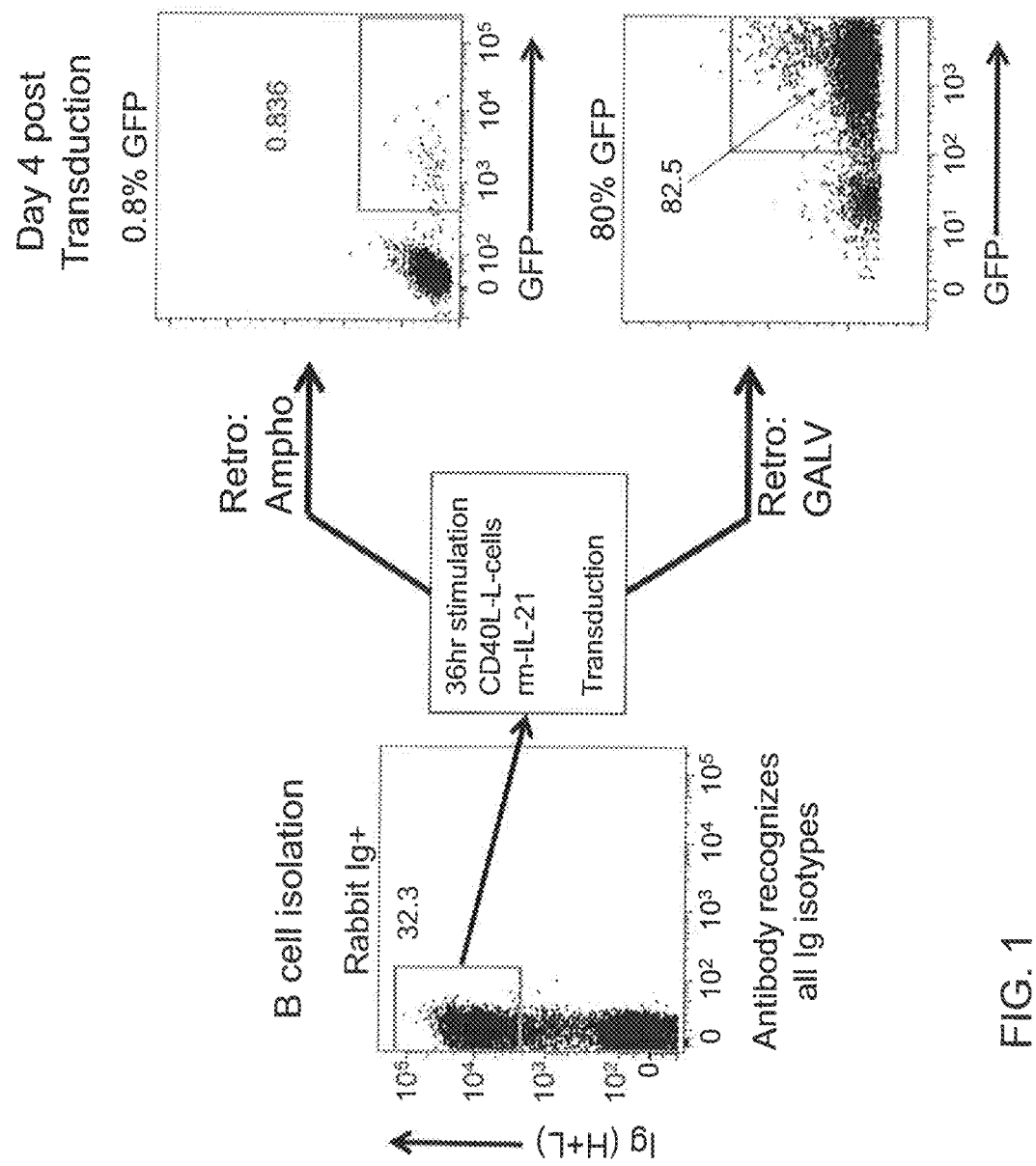
FIG. 1.
Figure 2:
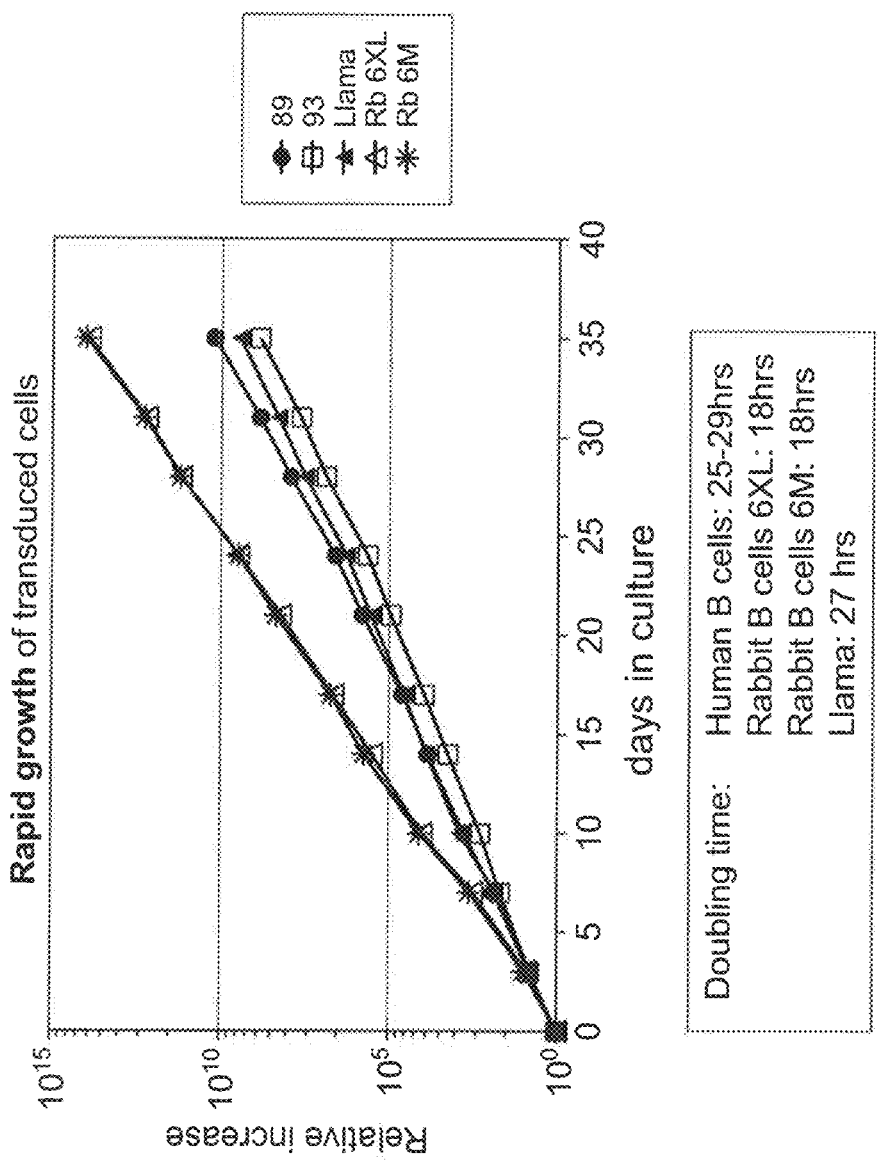
Figure 3:
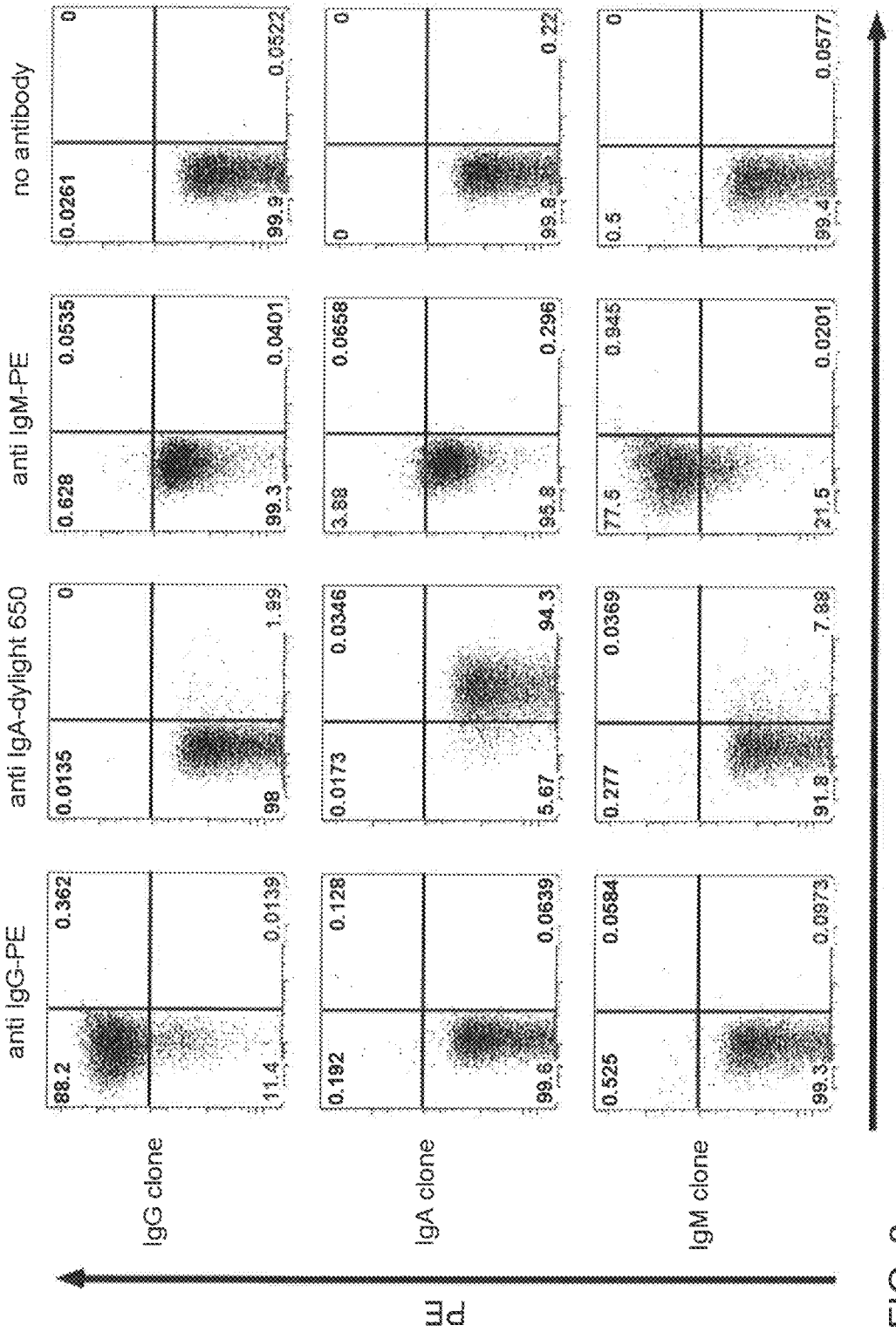
Figure 4:
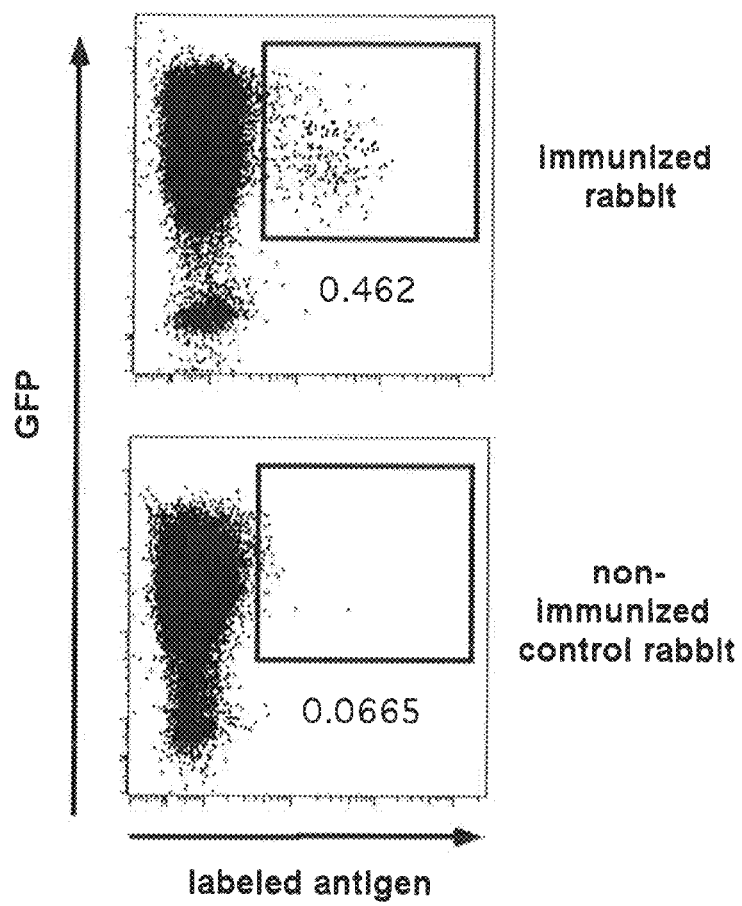
Figure 7:
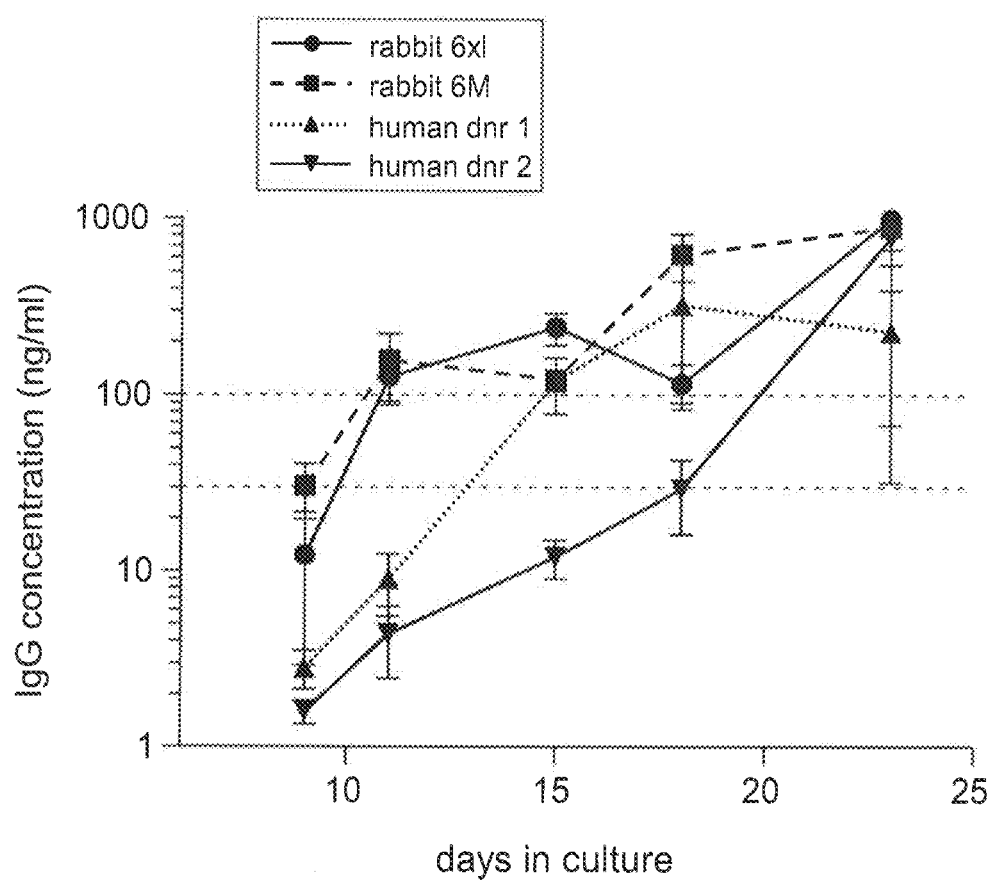
Figure 8:
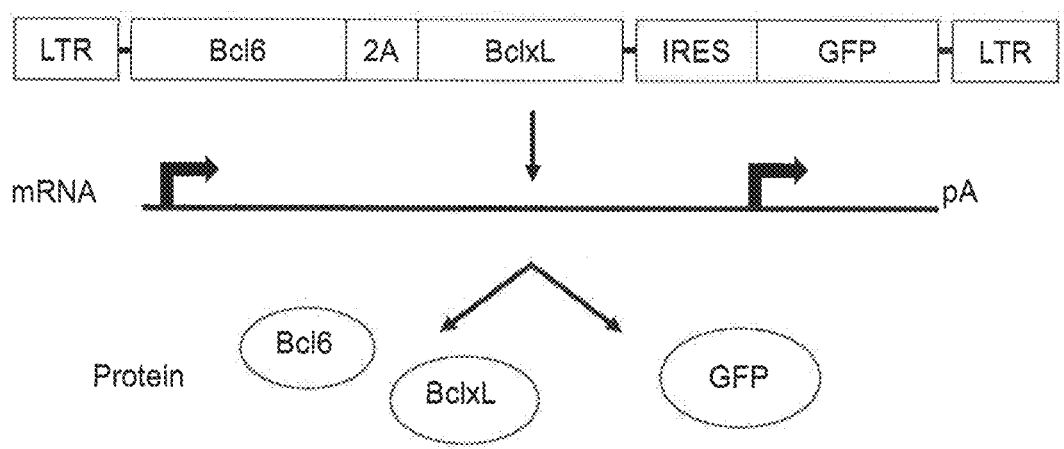
Figure 10:
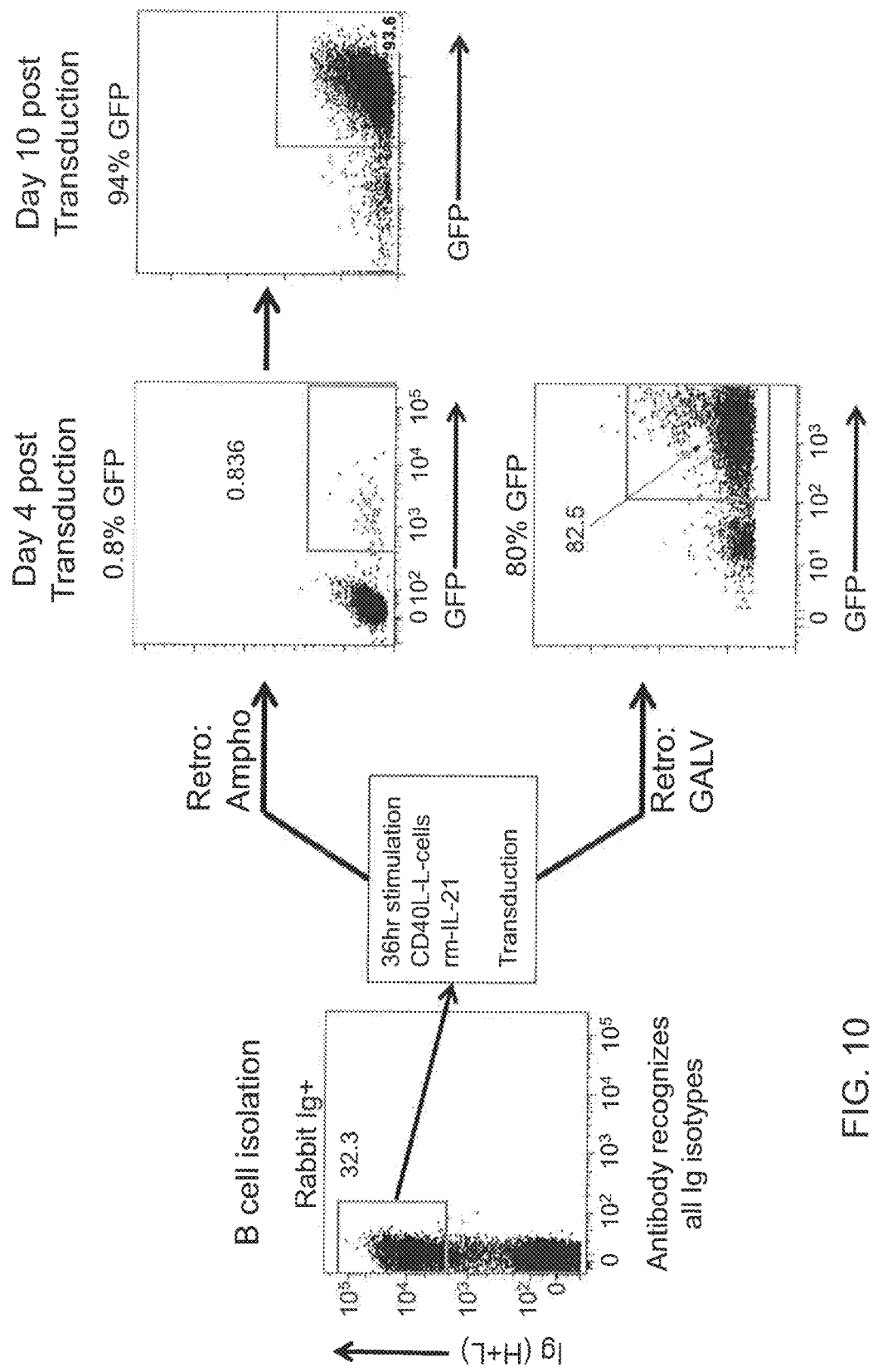
Figure 11:
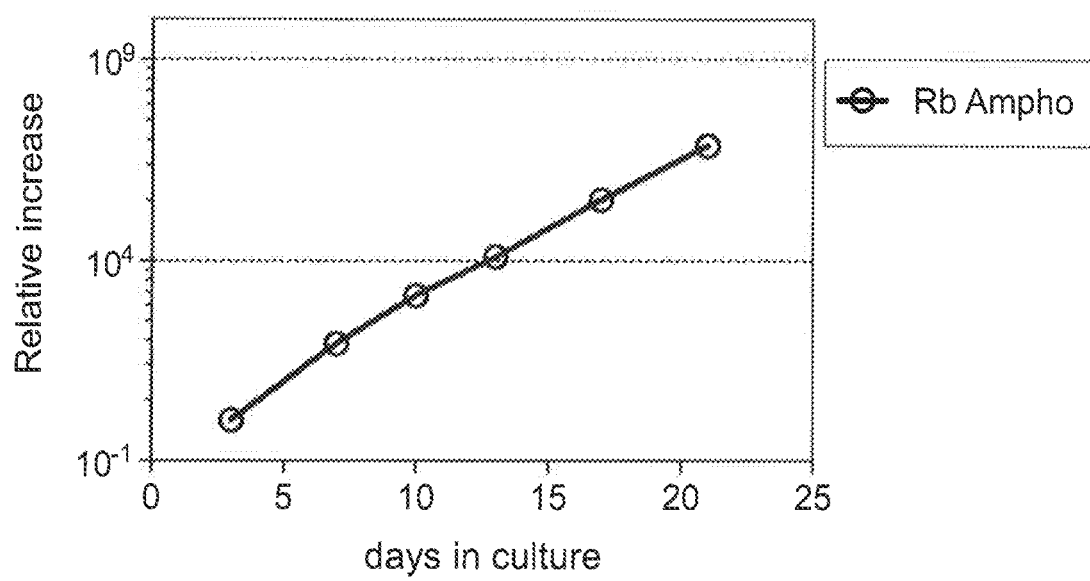

Transduction of rabbit memory B cells. Rabbit B cells were isolated from PBMCs based on Ig expression. Cells were activated for 36-40 hrs on CD40L L-cells with rm-IL-21. Cells were transduced with a retroviral vector containing BCL6 and Bcl-xL. Both GALV and amphotropic type retroviruses were tested. Transduced cells are then cultured on CD40L-L cells in the presence of recombinant mouse IL-21. After four days of culture the transduction efficiency was determined based on GFP expression. GALV typed retrovirus showed superior (80%) transduction efficiency compared to amphotropic (0.8%) typed retrovirus.

FIG. 2.

Growth curves were analyzed for rabbit B cells transduced with a retroviral vector containing BCL6 and Bcl-xL or a retroviral vector containing BCL6 and Mcl-1. For comparison growth curves were analysed in parallel B cells from llama cells and human cells from two different donors that were transduced with an identical retroviral vector containing BCL6 and Bcl-xL.

FIG. 3.

IgG, IgM and IgA surface immunoglobulin expression was detected using FACS on three different Bcl-6 Bcl-xL transduced rabbit B-cell clones.

FIG. 4.

Identification of antigen-specific rabbit B-cells within a pool of rabbit B cells with different specificities.

FIG. 5.

Antigen-specific rabbit antibodies were obtained against the different components of a human influenza vaccine containing 15 ug H1N1, 15 ug H3N2 and 15 ug infl B. Rabbits were immunized and boosted with the human influenza vaccine. B cells were immortalized and seeded at different densities in 384-well plates on CD40L-L cells in the presence of recombinant mouse IL-21. Antibodies present in the rabbit B cell culture supernatants were screened in ELISA for influenza-specificity.

Antigen-specific antibodies were observed for all the components of the vaccine.

FIG. 6.

Immortalized B cells from rabbits immunized with a human influenza vaccine containing 15 ug H1N1, 15 ug H3N2 and 15 ug infl B were stained with fluorescently labelled influenza proteins. B cells showing binding to the influenza proteins were sorted 1 cell per well in 384-well plates on CD40L-L cells in the presence of recombinant mouse IL-21 using a FACSAria sorter. Supernatants were screened in ELISA for influenza-specific antibodies. Antigen-specific antibodies were observed with a high frequency for the components of the vaccine that were used for antigen-specific sorting.

FIG. 7.

Antibody concentration in the supernatant of clonal B cells at different time points. Human, llama and rabbit transduced B cells were seeded 1 cell per well in the presence of irradiated CD40L-L cells and supplemented with mouse IL-21. Every 3-4 days CD40L-L cells and IL-21 were replenished. The IgG concentration was analyzed in ELISA for individual wells at different time points during culture. Each measurement was done on different wells. The rabbit B cells were either transduced with a retroviral vector containing BCL6 and Bcl-xL or a retroviral vector containing BCL6 and Mcl-1. All other cells (human and llama) were transduced with BCL6 and Bcl-xL.

FIG. 8.

Schematic representation of the vector used to transduce the rabbit and human B cells

FIG. 9.

Sequence of the extracellular domain of GALV SEATO envelope protein (bold) and the transmembrane domain of the GALV SEATO envelope protein (underlined), fused to the cytoplasmic domain of ampho envelope protein (italics+dotted-underlined).

FIG. 10.

Transduction of rabbit memory B cells and outgrowth of rabbit B cells transduced with amphotrophic type retrovirus. Rabbit B cells were isolated from PBMCs based on Ig expression. Cells were activated for 36-40 hrs on CD40L L-cells with rm-IL-21. Cells were transduced with a retroviral vector containing BCL6 and Bcl-xL. Both GALV and amphotropic type retroviruses were tested. Transduced cells were then cultured on CD40L-L cells in the presence of recombinant mouse IL-21. After four days of culture the transduction efficiency was determined based on GFP expression. GALV typed retrovirus showed superior (80%) transduction efficiency compared to amphotropic (0.8%) typed retrovirus. After 10 days 94% of rabbit B cells transduced with amphotrophic type retrovirus were immortalized based on GFP expression showing outgrowth of transduced cells over non-transduced cells.

FIG. 11.

A growth curve was analyzed for rabbit B cells transduced with a amphotrophic type retroviral vector containing BCL6 and Bcl-xL

REFERENCES

Christopherson, K. S. et al. PNAS 89, 6314-8 (1992)

Guzman, L. M. et al. Bacteriol 177, 4121-4130 (1995)

T. M. Kinsella, G. P. Nolan, Hum Gene Ther 7 (1996) 1405.

Kwakkenbos et al. Generation of stable monoclonal antibody-producing B cell receptor-positive human memory B cells by genetic programming. Nature Medicine (2010) vol. 16 (1) pp. 123-8

Lam et al. Improved gene transfer into human lymphocytes using retroviruses with the gibbon ape leukemia virus envelope. Human gene therapy 7 (1996) 1415-1422

A. L. Szymczak, C. J. Workman, Y. Wang, K. M. Vignali, S. Dilioglou, E. F. Vanin, D. A. A. Vignali, Nat Biotechnol 22 (2004) 589.

C. A. Wilson, M. V. Eiden, W. B. Anderson, C. Lehel, Z. Olah, J Virol 69 (1995) 534.

WO 2007/067046

The invention claimed is:

1. A method for obtaining antibodies comprising:
   inducing, enhancing and/or maintaining expression of Bcl-6, or a rabbit homologue thereof, in a rabbit B cell;
   inducing, enhancing and/or maintaining expression of at least one anti-apoptotic nucleic acid molecule in said B cell,
   culturing said B cell ex vivo to produce antibodies in a culture medium; and
   harvesting antibodies from the culture medium in an amount of at least 100 ng/ml culture medium within 10-14 days from the start of the culturing.

2. The method of claim 1, wherein said rabbit B cell is provided with:
   a nucleic acid molecule encoding Bcl-6 or a functional part or a functional derivative thereof, and/or
   at least one anti-apoptotic nucleic acid molecule.

3. The method of claim 1, wherein said rabbit B cell is provided with:
   a nucleic acid molecule encoding a non-rabbit Bcl-6 or a functional part or a functional derivative thereof, and/or
   at least one non-rabbit anti-apoptotic nucleic acid molecule.

4. The method of claim 1, wherein said rabbit B cell is provided with:
   a nucleic acid molecule encoding a rabbit Bcl-6 or a functional part or a functional derivative thereof, and/or
   at least one rabbit anti-apoptotic nucleic acid molecule.

5. The method of claim 1, wherein said rabbit B cell is provided with:
   a nucleic acid molecule encoding a non-rabbit Bcl-6 or a functional part or a functional derivative thereof, and
   at least one non-rabbit anti-apoptotic nucleic acid molecule.

6. The method of claim 1, wherein said rabbit B cell is provided with:
   a nucleic acid molecule encoding a human or murine Bcl-6 or a functional part or a functional derivative thereof, and/or
   at least one human or murine anti-apoptotic nucleic acid molecule.

7. The method of claim 1, wherein said rabbit B cell is provided with:
   a nucleic acid molecule encoding a human Bcl-6 or a functional part or a functional derivative thereof, and
   at least one human anti-apoptotic nucleic acid molecule.

8. The method of claim 3, wherein said non-rabbit nucleic acid molecules are human nucleic acid molecules.

9. The method of claim 1, wherein said rabbit B cell is provided with:
a nucleic acid molecule encoding a non-rabbit Bcl-6 or a functional part or a functional derivative thereof, and
at least one rabbit anti-apoptotic nucleic acid molecule.

10. The method of claim 1, wherein said rabbit B cell is provided with:
a nucleic acid molecule encoding a rabbit Bcl-6 or a functional part or a functional derivative thereof, and
at least one non-rabbit anti-apoptotic nucleic acid molecule.

11. The method of claim 1, wherein said at least one anti-apoptotic nucleic acid molecule comprises a gene of the Bcl2 family.

12. The method of claim 1, wherein said at least one anti-apoptotic nucleic acid molecule comprises a gene of the Bcl2 family selected from the group consisting of Bcl-xL, Mcl-1, Bcl-2, A1, Bcl-w, Bcl2L10, and rabbit homologues thereof and functional parts thereof and functional derivatives thereof.

13. The method of claim 1 further comprising: inducing, enhancing and/or maintaining expression of Blimp-1, or a rabbit homologue thereof, in said rabbit B cell.

14. The method of claim 1, further comprising providing said rabbit B cell with IL21 and CD40L.

15. The method of claim 14, wherein said IL21 is mouse or human IL21 and/or wherein said CD40L is mouse or human CD40.

16. The method of claim 1, comprising:
providing said rabbit B cell with a compound capable of directly or indirectly enhancing expression of Bcl-6, or expression of a rabbit homologue thereof; and/or
culturing said rabbit B cell in the presence of a compound capable of directly or indirectly enhancing expression of Bcl-6, or expression of a rabbit homologue thereof.

17. The method of claim 1, comprising:
providing said rabbit B cell with at least one compound capable of directly or indirectly enhancing expression of Bcl-XL and/or Mcl-1 and/or Bcl-2 and/or A1 and/or Bcl-w and/or Bcl2L10 and/or or a rabbit homologue thereof; and/or
culturing said rabbit B cell in the presence of at least one compound capable of directly or indirectly enhancing expression of Bcl-XL and/or Mcl-1 and/or Bcl-2 and/or A1 and/or Bcl-w and/or Bcl2L10 and/or a rabbit homologue thereof.

18. The method of claim 1, further comprising:
providing said rabbit B cell with at least one compound capable of directly or indirectly increasing expression of Blimp-1, or expression of a rabbit homologue of Blimp-1; and/or
culturing said rabbit B cell in the presence of at least one compound capable of directly or indirectly increasing expression of Blimp-1, or expression of a rabbit homologue of Blimp-1.

19. The method of claim 1, wherein antibodies are harvested from the culture medium within 11-12 days from the start of the culturing.

* * * * *

SEQUENCE LISTING

```
<160> NUMBER OF SEQ ID NOS: 4

<210> SEQ ID NO 1
<211> LENGTH: 632
<212> TYPE: PRT
<213> ORGANISM: Gibbon leukemia virus

<400> SEQUENCE: 1

Met Val Leu Leu Pro Gly Ser Met Leu Leu Thr Ser Asn Leu His His
1               5                   10                  15
```

-continued

```
Leu Arg His Gln Met Ser Pro Gly Ser Trp Lys Arg Leu Ile Ile Leu
        20              25              30
Leu Ser Cys Val Phe Gly Gly Gly Thr Ser Leu Gln Asn Lys Asn
        35              40              45
Pro His Gln Pro Met Thr Leu Thr Trp Gln Val Leu Ser Gln Thr Gly
 50              55              60
Asp Val Val Trp Asp Thr Lys Ala Val Gln Pro Pro Trp Thr Trp
 65              70              75              80
Pro Thr Leu Lys Pro Asp Val Cys Ala Leu Ala Ser Leu Glu Ser
                85              90              95
Trp Asp Ile Pro Gly Thr Asp Val Ser Ser Lys Arg Val Arg Pro
                100             105             110
Pro Asp Ser Asp Tyr Thr Ala Ala Tyr Lys Gln Ile Thr Trp Gly Ala
                115             120             125
Ile Gly Cys Ser Tyr Pro Arg Ala Arg Thr Arg Met Ala Ser Ser Thr
 130             135             140
Phe Tyr Val Cys Pro Arg Asp Gly Arg Thr Leu Ser Glu Ala Arg Arg
 145             150             155             160
Cys Gly Gly Leu Glu Ser Leu Tyr Cys Lys Glu Trp Asp Cys Glu Thr
                165             170             175
Thr Gly Thr Gly Tyr Trp Leu Ser Lys Ser Ser Lys Asp Leu Ile Thr
                180             185             190
Val Lys Trp Asp Gln Asn Ser Glu Trp Thr Gln Lys Phe Gln Gln Cys
                195             200             205
His Gln Thr Gly Trp Cys Asn Pro Leu Lys Ile Asp Phe Thr Asp Lys
        210             215             220
Gly Lys Leu Ser Lys Asp Trp Ile Thr Gly Lys Thr Trp Gly Leu Arg
225             230             235             240
Phe Tyr Val Ser Gly His Pro Gly Val Gln Phe Thr Ile Arg Leu Lys
                245             250             255
Ile Thr Asn Met Pro Ala Val Ala Val Gly Pro Asp Leu Val Leu Val
                260             265             270
Glu Gln Gly Pro Pro Arg Thr Ser Leu Ala Leu Pro Pro Leu Pro
        275             280             285
Pro Arg Glu Ala Pro Pro Ser Leu Pro Asp Ser Asn Ser Thr Ala
        290             295             300
Leu Ala Thr Ser Ala Gln Thr Pro Thr Val Arg Lys Thr Ile Val Thr
305             310             315             320
Leu Asn Thr Pro Pro Thr Thr Gly Asp Arg Leu Phe Asp Leu Val
                325             330             335
Gln Gly Ala Phe Leu Thr Leu Asn Ala Thr Asn Pro Gly Ala Thr Glu
                340             345             350
Ser Cys Trp Leu Cys Leu Ala Met Gly Pro Pro Tyr Tyr Glu Ala Ile
        355             360             365
Ala Ser Ser Gly Glu Val Ala Tyr Ser Thr Asp Leu Asp Arg Cys Arg
        370             375             380
Trp Gly Thr Gln Gly Lys Leu Thr Leu Thr Glu Val Ser Gly His Gly
385             390             395             400
Leu Cys Ile Gly Lys Val Pro Phe Thr His Gln His Leu Cys Asn Gln
                405             410             415
Thr Leu Ser Ile Asn Ser Ser Gly Asp His Gln Tyr Leu Leu Pro Ser
                420             425             430
```

```
Asn His Ser Trp Trp Ala Cys Ser Thr Gly Leu Thr Pro Cys Leu Ser
            435                 440                 445

Thr Ser Val Phe Asn Gln Thr Arg Asp Phe Cys Ile Gln Val Gln Leu
        450                 455                 460

Ile Pro Arg Ile Tyr Tyr Tyr Pro Glu Glu Val Leu Leu Gln Ala Tyr
465                 470                 475                 480

Asp Asn Ser His Pro Arg Thr Lys Arg Glu Ala Val Ser Leu Thr Leu
                485                 490                 495

Ala Val Leu Leu Gly Leu Gly Ile Thr Ala Gly Ile Gly Thr Gly Ser
            500                 505                 510

Thr Ala Leu Ile Lys Gly Pro Ile Asp Leu Gln Gln Gly Leu Thr Ser
            515                 520                 525

Leu Gln Ile Ala Ile Asp Ala Asp Leu Arg Ala Leu Gln Asp Ser Val
    530                 535                 540

Ser Lys Leu Glu Asp Ser Leu Thr Ser Leu Ser Glu Val Val Leu Gln
545                 550                 555                 560

Asn Arg Arg Gly Leu Asp Leu Leu Phe Leu Lys Glu Gly Gly Leu Cys
                565                 570                 575

Ala Ala Leu Lys Glu Glu Cys Cys Phe Tyr Ile Asp His Ser Gly Ala
            580                 585                 590

Val Arg Asp Ser Met Lys Lys Leu Lys Glu Lys Leu Asp Lys Arg Gln
            595                 600                 605

Leu Glu Arg Gln Lys Ser Gln Asn Trp Tyr Glu Gly Trp Phe Asn Asn
        610                 615                 620

Ser Pro Trp Phe Thr Thr Leu Leu
625                 630

<210> SEQ ID NO 2
<211> LENGTH: 21
<212> TYPE: PRT
<213> ORGANISM: Gibbon leukemia virus

<400> SEQUENCE: 2

Ser Thr Ile Ala Gly Pro Leu Leu Leu Leu Leu Leu Leu Ile Leu
1               5                   10                  15

Gly Pro Cys Ile Ile
            20

<210> SEQ ID NO 3
<211> LENGTH: 33
<212> TYPE: PRT
<213> ORGANISM: Gibbon leukemia virus

<400> SEQUENCE: 3

Asn Arg Leu Val Gln Phe Val Lys Asp Arg Ile Ser Val Val Gln Ala
1               5                   10                  15

Leu Val Leu Thr Gln Gln Tyr His Gln Leu Lys Pro Ile Glu Tyr Glu
            20                  25                  30

Pro

<210> SEQ ID NO 4
<211> LENGTH: 686
<212> TYPE: PRT
<213> ORGANISM: Artificial Sequence
<220> FEATURE:
<223> OTHER INFORMATION: fused GALV protein

<400> SEQUENCE: 4
```

```
Met Val Leu Leu Pro Gly Ser Met Leu Leu Thr Ser Asn Leu His
1               5                   10                  15

Leu Arg His Gln Met Ser Pro Gly Ser Trp Lys Arg Leu Ile Ile Leu
            20                  25                  30

Leu Ser Cys Val Phe Gly Gly Gly Thr Ser Leu Gln Asn Lys Asn
        35                  40                  45

Pro His Gln Pro Met Thr Leu Thr Trp Gln Val Leu Ser Gln Thr Gly
    50                  55                  60

Asp Val Val Trp Asp Thr Lys Ala Val Gln Pro Trp Thr Trp
65                  70                  75                  80

Pro Thr Leu Lys Pro Asp Val Cys Ala Leu Ala Ser Leu Glu Ser
                85                  90                  95

Trp Asp Ile Pro Gly Thr Asp Val Ser Ser Lys Arg Val Arg Pro
            100                 105                 110

Pro Asp Ser Asp Tyr Thr Ala Ala Tyr Lys Gln Ile Thr Trp Gly Ala
            115                 120                 125

Ile Gly Cys Ser Tyr Pro Arg Ala Arg Thr Arg Met Ala Ser Ser Thr
    130                 135                 140

Phe Tyr Val Cys Pro Arg Asp Gly Arg Thr Leu Ser Glu Ala Arg Arg
145                 150                 155                 160

Cys Gly Gly Leu Glu Ser Leu Tyr Cys Lys Glu Trp Asp Cys Glu Thr
                165                 170                 175

Thr Gly Thr Gly Tyr Trp Leu Ser Ser Ser Lys Asp Leu Ile Thr
            180                 185                 190

Val Lys Trp Asp Gln Asn Ser Glu Trp Thr Gln Lys Phe Gln Gln Cys
    195                 200                 205

His Gln Thr Gly Trp Cys Asn Pro Leu Lys Ile Asp Phe Thr Asp Lys
    210                 215                 220

Gly Lys Leu Ser Lys Asp Trp Ile Thr Gly Lys Thr Trp Gly Leu Arg
225                 230                 235                 240

Phe Tyr Val Ser Gly His Pro Gly Val Gln Phe Thr Ile Arg Leu Lys
                245                 250                 255

Ile Thr Asn Met Pro Ala Val Ala Val Gly Pro Asp Leu Val Leu Val
            260                 265                 270

Glu Gln Gly Pro Pro Arg Thr Ser Leu Ala Leu Pro Pro Pro Leu Pro
    275                 280                 285

Pro Arg Glu Ala Pro Pro Ser Leu Pro Asp Ser Asn Ser Thr Ala
    290                 295                 300

Leu Ala Thr Ser Ala Gln Thr Pro Thr Val Arg Lys Thr Ile Val Thr
305                 310                 315                 320

Leu Asn Thr Pro Pro Thr Thr Gly Asp Arg Leu Phe Asp Leu Val
                325                 330                 335

Gln Gly Ala Phe Leu Thr Leu Asn Ala Thr Asn Pro Gly Ala Thr Glu
            340                 345                 350

Ser Cys Trp Leu Cys Leu Ala Met Gly Pro Pro Tyr Tyr Glu Ala Ile
        355                 360                 365

Ala Ser Ser Gly Glu Val Ala Tyr Ser Thr Asp Leu Asp Arg Cys Arg
    370                 375                 380

Trp Gly Thr Gln Gly Lys Leu Thr Leu Thr Glu Val Ser Gly His Gly
385                 390                 395                 400

Leu Cys Ile Gly Lys Val Pro Phe Thr His Gln His Leu Cys Asn Gln
            405                 410                 415

Thr Leu Ser Ile Asn Ser Ser Gly Asp His Gln Tyr Leu Leu Pro Ser
```

-continued

```
                    420                 425                 430
Asn His Ser Trp Trp Ala Cys Ser Thr Gly Leu Thr Pro Cys Leu Ser
        435                 440                 445

Thr Ser Val Phe Asn Gln Thr Arg Asp Phe Cys Ile Gln Val Gln Leu
        450                 455                 460

Ile Pro Arg Ile Tyr Tyr Pro Glu Glu Val Leu Leu Gln Ala Tyr
465             470                 475                 480

Asp Asn Ser His Pro Arg Thr Lys Arg Glu Ala Val Ser Leu Thr Leu
        485                 490                 495

Ala Val Leu Leu Gly Leu Gly Ile Thr Ala Gly Ile Gly Thr Gly Ser
        500                 505                 510

Thr Ala Leu Ile Lys Gly Pro Ile Asp Leu Gln Gln Gly Leu Thr Ser
        515                 520                 525

Leu Gln Ile Ala Ile Asp Ala Asp Leu Arg Ala Leu Gln Asp Ser Val
        530                 535                 540

Ser Lys Leu Glu Asp Ser Leu Thr Ser Leu Ser Glu Val Val Leu Gln
545             550                 555                 560

Asn Arg Arg Gly Leu Asp Leu Leu Phe Leu Lys Glu Gly Gly Leu Cys
                565                 570                 575

Ala Ala Leu Lys Glu Glu Cys Cys Phe Tyr Ile Asp His Ser Gly Ala
                580                 585                 590

Val Arg Asp Ser Met Lys Lys Leu Lys Glu Lys Leu Asp Lys Arg Gln
        595                 600                 605

Leu Glu Arg Gln Lys Ser Gln Asn Trp Tyr Glu Gly Trp Phe Asn Asn
        610                 615                 620

Ser Pro Trp Phe Thr Thr Leu Leu Ser Thr Ile Ala Gly Pro Leu Leu
625             630                 635                 640

Leu Leu Leu Leu Leu Leu Ile Leu Gly Pro Cys Ile Ile Asn Arg Leu
                645                 650                 655

Val Gln Phe Val Lys Asp Arg Ile Ser Val Val Gln Ala Leu Val Leu
        660                 665                 670

Thr Gln Gln Tyr His Gln Leu Lys Pro Ile Glu Tyr Glu Pro
        675                 680                 685
```